US007205454B2

(12) United States Patent
Vanderkimpen et al.

(10) Patent No.: US 7,205,454 B2
(45) Date of Patent: Apr. 17, 2007

(54) CORN ROOT PREFERENTIAL PROMOTERS AND USES THEREOF

(75) Inventors: Greet Vanderkimpen, St-Amandsberg (BE); Gerben Van Eldik, Zwijnaarde (BE); Frank Meulewaeter, Melle (BE)

(73) Assignee: Bayer BioScience N.V., Ghent (BE)

( * ) Notice: Subject to any disclaimer, the term of this patent is extended or adjusted under 35 U.S.C. 154(b) by 537 days.

(21) Appl. No.: 10/623,500

(22) Filed: Jul. 22, 2003

(65) Prior Publication Data

US 2004/0133945 A1    Jul. 8, 2004

Related U.S. Application Data

(60) Provisional application No. 60/399,383, filed on Jul. 31, 2002.

(51) Int. Cl.
*C12N 15/82* (2006.01)
*A01H 5/10* (2006.01)
*C07H 21/04* (2006.01)

(52) U.S. Cl. ............... 800/287; 536/24.1; 435/320.1; 435/419; 435/468; 800/298

(58) Field of Classification Search ............... None
See application file for complete search history.

(56) References Cited

U.S. PATENT DOCUMENTS

| | | | |
|---|---|---|---|
| 5,561,236 A | 10/1996 | Leemans et al. | |
| 5,633,363 A | 5/1997 | Colbert et al. | |
| 5,641,664 A | 6/1997 | D'Halluin et al. | |
| 5,712,126 A | 1/1998 | Weissman et al. | |
| 5,744,336 A | 4/1998 | Hodges et al. | |
| 5,767,367 A | 6/1998 | Dudits et al. | |
| 5,792,936 A | 8/1998 | Dudits et al. | |
| 6,023,013 A | 2/2000 | English et al. | |
| 6,074,877 A | 6/2000 | D'Halluin et al. | |
| 6,140,553 A | 10/2000 | D'Halluin | |

FOREIGN PATENT DOCUMENTS

| WO | WO 96/10083 | 4/1996 |
|---|---|---|
| WO | WO 97/40162 | 10/1997 |
| WO | WO 97/44448 | 11/1997 |
| WO | WO 99/53050 | 10/1999 |
| WO | WO 00/15662 | 3/2000 |
| WO | WO 00/26378 | 5/2000 |
| WO | WO 00/32799 | 6/2000 |
| WO | WO 00/70066 | 11/2000 |
| WO | WO 00/70068 | 11/2000 |
| WO | WO 01/87931 A2 | 11/2001 |

OTHER PUBLICATIONS

Oommenn et al 1994, The Plant Cell 6:1789-1803.*
Fiedler U. et al. 1993, Plant Mol Biol. 22(4):669-79.*
Kim et al. 1994, Plant Molecular Biology 24: 105-117.*
Clone MEST23-CO7.
Clone MEST523-G12.
Clone hg88e04.b8.
Clone hg88e04.g8.
Marc De Block et al., "RNA—RNA in Situ Hybridization Using Digoxigenin-Labeled Probes: The Use of High-Molecular-Weight Polyvinyl Alcohol in the Alkaline Phosphatase Indoxyl-Nitroblue Tetrazolium Reaction" *Analytical Biochemistry*, vol. 215, pp. 86-88 (1993), Academic Press, Inc., London, England.
Lining Guo et al., "*Photorhabdus luminescens* W-14 Insecticidal Activity Consists of at Least Two Similar but Distinct Proteins", *The Journal of Biological Chemistry*, vol. 274, No. 14, pp. 9836-9842 (Apr. 2, 1999) The American Society for Biochemistry and Molecular Biology, Inc., Baltimore, Maryland, USA.
Kentaro Irie et al, "Transgenic Rice Established to Express Corn Cystatin Exhibits Strong Inhibitory Activity Against Insect Gut Proteinases", *Plant Molecular Biology*, vol. 30, pp. 149-157 (1996), Kluwer Academic Publishers, Dordrecht, Holland.
Yao-Guang Liu et al., "Efficient Isolation and Mapping of *Arabidopsis thaliana* T-DNA Insert Junctions by Thermal Asymmetric Interfaced PCR", *The Plant Journal*, vol. 8, No. 3, pp. 457-463, (1995) Blackwell Sciences, Oxford, England.
Yatindra Prashar et al., "READS: A Method for Display of 3'-End Fragments of Restriction Enzyme-Digested cDNAs for Analysis of Differential Gene Expression", *Methods in Enzymology*, vol. 303, pp. 258-272 (1999), Academic Press, New York, New York USA.
Yuan Zhao et al., "Two Wound-Inducible Soybean Cysteine Proteinase Inhibitors Have Greater Insect Digestive Proteinase Inhibitory Activities Than a Constitutive Homolog", *Plant Physiol.*, vol. 111, pp. 1299-1306 (1996) American Society of Plant Physiologists, Lancaster, PA, USA.

* cited by examiner

*Primary Examiner*—Ashwin Mehta
*Assistant Examiner*—Li Zheng
(74) *Attorney, Agent, or Firm*—Buchanan Ingersoll & Rooney PC

(57) ABSTRACT

The invention relates to the isolation of promoters from corn capable of directing transcription of an operably linked foreign DNA sequence preferentially, selectively or exclusively in the roots of plants, such as corn plants. The invention also relates to the use of chimeric genes for the preferential or selective expression of biologically active RNA of interest in the roots of plants, such as corn plants. Plants, such as corn plants, comprising corn root preferential or selective promoters operably linked to a foreign DNA sequence which, upon transcription, yield biologically active RNA preferentially or selectively in the roots of plants are also provided.

13 Claims, 6 Drawing Sheets

```
GL12   ------------------------------------------------------------
GL4    CAAGGAGAGAGAGCATATATATCCACCGATCATGATGAAGGGTGGCAGCAAGAAGAAGTGGCCGGTGCGGCGGC
GL5    CAATCAGATAGAGAGCATAGT-----CGATCATG---AAGGGTGGCA---AGAAGGAAGTGGCCGGTG-----C

GL12   ------------------------------------------------------------
GL4    GGTGGTGGCCATACTGCTGTGTTCTGCAGCTGATGGCAGCTCCACCGACGGCCATGCCGCCCCGCTCGCCGCGG
GL5    GGTGGTGGCCATACTGCTGTGTTCTGCAGCTCATGGCAGCTCCACCGACGGCCATGCCGCCCCGCTCGCCGCGG

GL12   ------------------------------------------------------------
GL4    AGCCGTGCCGGATGGCTCCCTCGCCACGACGCCCAAGGTGACGATGCTGTCAGCCACGCTGTGCTACACGGGGGA
GL5    AGCCGTGCCGGATGGCTCCCTCGCCACGACGCCCAAGGTGACGATGCTGTCAGCCACGCTGTGCTACACGGGGGA

GL12   ------------------------------------------------------------
GL4    GACATGCAAATACATTACCTGCCTCACTCCTGCTTGCCTCCTGTAACTATGATGATCGTCGCTGCTACATCATATT
GL5    GACATGCAAATACATTGGCTGCCTCACTCCTGCCTCCTGCTTGCCTCCTGCAACTATAGTGATCGTCTATGCTACATCATATT

GL12   ------------------------------------------------------------
GL4    TACTCCTGCTGCTGTGAGGCCATTCGTGTACGTGAATGAAGCCACTACTCTCACACAGCATGCCGGC
GL5    TACTCCCTGTG---CTTGAGGCCATTCCGCG------AAGCCACAACT--CTTACAATATGCGCCGGC

GL12   -----------------------------TTTTGTTTAAGNTGT-CGGG--CACAGCG--
GL4    CGAGCAGCGTGCGTACGTATATATATACGCTCTACCTCGTGAGCTTTGTTCGAGTGATACGTGTTTCAAGGCATC
GL5    CG-----CGCTCGCCTCTCGTGAGCTTCCTGTTCAAGTGATGATGCATGTTCAAGGCATCCATGGCGACGACG--

GL12   ------------------------------------------------------------
GL4    CGGCCCAGCATGAATGNTTATGAACGGAAATGTGTTAGTCGTCGTGTCAGGCAGCAACCGGCAGCAGAAGGGGTGTT
GL5    CATCCATCCATGGATGCTTATGTGTTATGTTAGTCGTCGTGTT--CAGGGAACCGGCAA---GAAGGGGTGTT

GL12   ------------------------------------------------------------
GL4    --ACGATGCTT---TACGTATATGCTATTAAT--TAGCCGTGT--CAGGGAACCGGACA---GAAGGGGTGTT
GL5

GL12   GTATTATATATATTTACGTCTTCTGGTGATTAAATAATAAAGGGGCATGTTGGATGTGTGCAAAA
GL4    GTATTATATATATTNACGTCTTCTGGTGATTAAATAATAAAGGGGCATGTTGGATGTGTGCAAAA
GL5    GTTTTAT----ATTTACGTCTTCTGGTGATCAAATAAAGGGGAAATATATGTTGGATGTGTGTAAAA
```

Fig. 1

```
  1 TACTACAGAT AACACGACAG TTAACGAGCG GGTATGGGTT GTTTCCTTTG AGCACTGTTG
 61 TTCTCTAGAA TCTCTGAATC TCTCTCTGTC TTGATGACAC CGAGCGGAAA TAGCAGTTGG
121 AAGAGGTGAT TGGGCTTCAG CGCGCGATCC AACCCAAGTG GGTTCCACAA CGTGAACCTC
181 ATGCAGCTTA AAATACAGCC AGTTGTGATC CATCTGCCAC AGCTGTTTCT ACCTCAGATG
241 TGCTACACAG TGTATTACCT GTTTCTACCT CGCAGATGTG CTACACAGTT GCTTATGACT
301 GCCTATAAAA TGGCCCGGGAT CGGTGAGGCT GCTGGAACCA AGGAGAGAGA GCATATATAT
361 CCACCGATCC ATGGCATG
```

Fig. 2

```
   1 CGGGATCCCG GCTTTCTGCA CTGGACGTAG TGTACTTTAT ACTTGAAACT TGTATAAATT
  61 TGTGTCTTTT ATACTCCCTC AGTTTGAAAT ATAGTTCTTT CTAGCCTCTT TTTTCCGTC
 121 CACACTCATT TGAATGATAA TAAATATAGA TATACATACA AACTATATTC ATAGTTAAT
 181 TAATAAATGT ATATTTAGTC TAAAATGAAA TATATTTTAC CCATCGTATT CCTTATGCAT
 241 GAAATGTTGA TCTACTTGTC TGATGGAAAA ATACTATGAC GTTGTTGTAC CAGACCGCAC
 301 CTAAATCAAA CTGTTTTCAG AGATGGCCAT TCTATTATTG TAGATTTGTG ATACGTACGA
 361 TGTACTTTTT TATCCATAAA ATACCGTACC ATTATGATAT GGATATCTTG ATGAGAGGGA
 421 CTCATTATCT CTCTCTATAT ATATAAACAC CTATATATCA AACAGGCATC AAGAAAAATA
 481 GATGATTTTT TTTCTGAAGG TAGAGTGACA GAAGCAGCTG AAGTGTGAGT CTTTTTGTTT
 541 CAATTTTATA ATGTGTAAAG AAAATGACGC CAATGAAATA TGTGTCTGGG CTGACGTGTT
 601 GTTTGGTGAA AGCCAATTTT GTTGTATATA GGGGGCCAG AGCCCAGTTG TATTGTTGC
 661 CCGGACTGGC GCCAAAAAAA AAAATCCGA TAGTACTATT CCGCTAACTG TGTCACACTT
 721 TATCTAAAAT TAGTCATCCA AATTAAAGAA CTAACCTTAG ATACAAAAAA TTAAACAAAG
 781 TATGACAAGT TAGGTAGCAA ACTAAACTAA AGAGGATAAC ACAACAGTTA ACCGTCGACG
 841 TGCGCGGCCT GAATTACTA CTACAGATAA CACGACAGTT AACGAGCGGG TATGGGTTGT
 901 TTTCCTTGAG CACTGTTGTT CTCTAGAATC TCTCTGTCTT GATGACACCG
 961 AGCGGAAATA GCAGTTGGAA GAGGTGATTG GGCTTCAGCG CGCGATCCAA CCCAAGTGGG
1021 TTCCACAACG TGAACCTCAT GCAGCTTAAA ATACAGCCAG TTGTGATCCA TCTGCCACAG
1081 CTGTTTCTAC CTCAGAGTGT CTACACAGTG CTACACCTGT TTCTACCTCG CAGATGTGCT
1141 ACACAGTTGC TTATGACTGC CTATAAAATG GCCGGGATCG GTGAGGCTGC TGGAACCAAG
1201 GAGAGAGAGC ATATATATCC ACCGATCCAT GGCATG
```

Fig. 3

```
   1  GGCGGAATTT CATACTCATT ATATACGATG ATACACCATC ATACATAGTG ACATGACATA
  61  CAATTAAAAG CAGAGATATA GAAAGAGCTT ATGGGAGATG GTAGAGTTTC ATAGAGATAA
 121  AATTCTATAT ATACAATTAC CTAGTTTAAA TATGGTGTGA CAACATGGAA AACATTGTAC
 181  CGAAGCTCAC CGCTGAAAAT GGCCTTACAA AACTGAAAAG AAGATGTCAC TTGTTGTGAA
 241  GCTCACCGAT GAAACTGGCC TAACAAAACT GAAACAAAAA GATCTCATCT CACTTGTTCT
 301  GAAGCTCACC ACTAAGAATG ACCTTACAAA ACTGAAACAA AAAGATGTCA CTTGTTCTAA
 361  AGCTCACCAC TGAGAAAGGC CTTACAAAAC TAAAACAAAA AAAATATGTC ACATGTTCTG
 421  AAGCTCACCA CTGAGAATGG CCTTACAAAA CTGAAACAAA AATATGTCAT TTGTTTAGCT
 481  TGTCACTCTA CTTTAGGAAA ACAAAAAATCA TCGATATGTT TTTCTTGATG CCTGCTCGAT
 541  ATGGTGTTA TATATATATA TATATATAAT GTTCATAAAT ATATGACATC GCTGACTTTT
 601  TAAAAAACTT TAATCACTTG TCTTATTTAA AAAATAATGA GTTGTCATTT ATTTTTGTG
 661  TGGTTTGTTT TATCACTTAA GGTAGTTTGT GCTTAATTAA AATTTATAC TTTTGAATAA
 721  GATAAATGT CAAAGTTTTT TAAAAAATC AACATGTCAT ATATCTGTGA ACGGAGGTTG
 781  TATTACAGAA TGTGCGACGT ACACGCTACC CAACAAACAT CAACAAACAT TGGTACTGG
 841  AATTTTGCTC TTTGCGCATA GAATCCAATA CATAAAAATA GTATAGGCAG CGAACCAAAC
 901  ACGTCCCAAG TTTTATAATT TGTAAAGAAA ATGACAGCAT TTAAATATGA TAACACAATA
 961  ATTAACCAGC GGGTAAGGGT AGTTTTCGTT GAGCACTGTT GCGGTTTAGA ATCGCTGGAC
1021  CTGCGTGTTT ATGAGACACA GCGGGTAGCA GTTGGAAGAG ATGATTGGGC TAGCTAGCTT
1081  GAGCGATTCA GTCATCAACC CCAATATTGT TCCATTGCTG CATGCACATT TATCTATACC
1141  ACGACGACAC AACGTGAACC TCGTGCAGCT TTTTAAAATA CAGCCAGTTG TGATCCATCT
1201  ACCTGTCTGT CAGACGTGCT ACAGCCTACA GTTTAGTGAC TGCTGCCTAT AAAATGGCTG
1261  GCTGCTGGAG CAAAGCCAAA CCAATCAGAT AGAGAGCATA GTCGATCCAT GGCATG
```

Fig. 4

SEQUENCE LISTING

```
<160> NUMBER OF SEQ ID NOS: 32

<210> SEQ ID NO 1
<211> LENGTH: 378
<212> TYPE: DNA
<213> ORGANISM: Zea mays
<220> FEATURE:
<221> NAME/KEY: misc_feature
<222> LOCATION: (1)..(338)
<223> OTHER INFORMATION: promoter
<220> FEATURE:
<221> NAME/KEY: misc_feature
<222> LOCATION: (339)..(370)
<223> OTHER INFORMATION: 5' UTR

<400> SEQUENCE: 1
tactacagat aacacgacag ttaacgagcg ggtatgggtt gttttccttg agcactgttg      60
ttctctagaa tctctgaatc tctctctgtc ttgatgacac cgagcggaaa tagcagttgg     120
aagaggtgat tgggcttcag cgcgcgatcc aacccaagtg ggttccacaa cgtgaacctc     180
atgcagctta aaatacagcc agttgtgatc catctgccac agctgtttct acctcagatg     240
tgctacacag tgtattacct gtttctacct cgcagatgtg ctacacagtt gcttatgact     300
gcctataaaa tggccgggat cggtgaggct gctggaacca aggagagaga gcatatatat     360
ccaccgatcc atggcatg                                                   378

<210> SEQ ID NO 2
<211> LENGTH: 1236
<212> TYPE: DNA
<213> ORGANISM: Zea mays
<220> FEATURE:
<221> NAME/KEY: misc_feature
<222> LOCATION: (11)..(1196)
<223> OTHER INFORMATION: promoter
<220> FEATURE:
<221> NAME/KEY: misc_feature
<222> LOCATION: (1197)..(1228)
<223> OTHER INFORMATION: 5' UTR

<400> SEQUENCE: 2
cgggatcccg gctttctgca ctggacgtag tgtactttat acttgaaact tgtataaatt      60
tgtgtctttt atactccctc agtttgaaat atagttcttt ctagcctctt tttttccgtc     120
cacactcatt tgaatgataa taaatataga tatacataca aactatattc ataggttaat     180
taataaatgt atatttagtc taaaatgaaa tatatttac ccatcgtatt ccttatgcat      240
gaaatgttga tctacttgtc tgatggaaaa atactatgac gttgttgtac cagaccgcac     300
ctaaatcaaa ctgttttcag agatggccat tctattattg tagatttgtg atacgtacga     360
tgtacttttt tatccataaa ataccgtacc attatgatat ggatatcttg atgagaggga     420
```

```
ctcattatct ctctctatat atataaacac ctatatatca aacaggcatc aagaaaaata    480
gatgattttt ttttctgaag tagagtgaca gaagcagctg aagtgtgagt cttttgttt    540 caattttata atgtgtaaag aaaatgacgc caatgaaata tgtgtctggg ctgacgtgtt    600
gtttggtgaa agccaattt gttgtatata gggggccag agcccagttg tatttgttgc    660
ccggactggc gccaaaaaaa aaaatccgga tagtactatt ccgctaactg tgtcacactt    720
tatctaaaat tagtcatcca aattaaagaa ctaaccttag atacaaaaaa ttaaacaaag    780
tatgacaagt taggtagcaa actaaactaa agaggataac acaacagtta accgtcgacg    840
tgcgcggcct gaatttacta ctacagataa cacgacagtt aacgagcggg tatgggttgt    900
tttccttgag cactgttgtt ctctagaatc tctgaatctc tctctgtctt gatgacaccg    960
agcggaaata gcagttggaa gaggtgattg ggcttcagcg cgcgatccaa cccaagtggg   1020
ttccacaacg tgaacctcat gcagcttaaa atacagccag ttgtgatcca tctgccacag   1080
ctgtttctac ctcagatgtg ctacacagtg tattacctgt ttctacctcg cagatgtgct   1140
acacagttgc ttatgactgc ctataaaatg gccgggatcg gtgaggctgc tggaaccaag   1200
gagagagagc atatatatcc accgatccat ggcatg                             1236

<210> SEQ ID NO 3
<211> LENGTH: 592
<212> TYPE: DNA
<213> ORGANISM: Artificial
<220> FEATURE:
<223> OTHER INFORMATION: cDNA of GL4 transcript
<220> FEATURE:
<221> NAME/KEY: misc_feature
<222> LOCATION: (540)..(540)
<223> OTHER INFORMATION: n at position 540 represents any nucleotide

<400> SEQUENCE: 3
caaggagaga gagcatatat atccaccgat catgatgaag ggtggcagca agaaggaagt     60
ggccggtgcg gcggcggtgg tggccatact gctggttctg cagctgatgg cagctccacc    120
gacggccatg gccgcccgct cgccgcgcgg agccgtgccg gatggctccc tcgccacgac    180
gcccaaggtg acgatgctgt cagccacgct gtgctacacg ggggagacat gcaaatacat    240
tacctgcctc actcctgctt gctcctgtaa ctatgatgat cgtcgctgct acatcatatt    300
tactcctgct gctgcttgag gccattctgt gtacgtgaat gaagccacta ctactctcac    360
acagcatgcg ccgccgacg acgtgcgtac gtatatatat acgctctacc tcgtgagctt    420
ttgttcgagt gatacgtgtt tcaaggcatc catccatcca tggatgctta tgtacgtata    480
tgtgttagtc gtgtgtcagg caaccgggca gcagaagggg gtgttgtatt atatatattn    540
acgtcttctg gtgattaaat aataaagggg ggcatgttgg atgtgtgcaa aa            592

<210> SEQ ID NO 4
<211> LENGTH: 95
<212> TYPE: PRT
<213> ORGANISM: Zea mays

<400> SEQUENCE: 4

Met Met Lys Gly Gly Ser Lys Lys Glu Val Ala Gly Ala Ala Ala Val
1               5                   10                  15

Val Ala Ile Leu Leu Val Leu Gln Leu Met Ala Ala Pro Pro Thr Ala
            20                  25                  30

Met Ala Ala Arg Ser Pro Arg Gly Ala Val Pro Asp Gly Ser Leu Ala
        35                  40                  45
```

```
Thr Thr Pro Lys Val Thr Met Leu Ser Ala Thr Leu Cys Tyr Thr Gly
        50                  55                  60

Glu Thr Cys Lys Tyr Ile Thr Cys Leu Thr Pro Ala Cys Ser Cys Asn
 65                  70                  75                  80

Tyr Asp Asp Arg Arg Cys Tyr Ile Ile Phe Thr Pro Ala Ala Ala
                85                  90                  95

<210> SEQ ID NO 5
<211> LENGTH: 535
<212> TYPE: DNA
<213> ORGANISM: Artificial
<220> FEATURE:
<223> OTHER INFORMATION: cDNA of GL5 transcript
<220> FEATURE:
<221> NAME/KEY: misc_feature
<222> LOCATION: (82)..(82)
<223> OTHER INFORMATION: n represents any nucleotide

<400> SEQUENCE: 5
ccaatcagat agagagcata gtcgatcatg aagggtggca agaagaaagt ggccggtgcg    60
gtggtggcca tactgctggt tntgcagctc atggcagctc caccgacggc catggccgcc   120
cgctcgccgc gcggagccgt gccggatggc tccctcgcca cgacgcccaa ggtgacgatg   180
ctgtcggcca cgctgtgcta cacggggag acatgcaaat acattggctg cctcactcct    240
gcttgctcct gcaactatag tgatcgtcta tgctacatca tatttactcc tgttgcttga   300
ggccattccg cgaagccaca actcttacaa tatgcatgcg ccggccgacg acgacgcgcg   360
ctgcctctcg tgagcttctg ttcaagtgat gcatgtttca aggcatccat ggatgcttta   420
cgtatatgcg tattaattag ccgtgtcagg gaaccggaca gaaggggtg ttgttttata    480
tttacgtctt ctggtgatca aataaagggg aaatatatgt tggatgtgtg caaaa         535

<210> SEQ ID NO 6
<211> LENGTH: 90
<212> TYPE: PRT
<213> ORGANISM: Zea mays

<400> SEQUENCE: 6

Met Lys Gly Gly Lys Lys Glu Val Ala Gly Val Val Ala Ile Leu
 1               5                  10                  15

Leu Val Leu Gln Leu Met Ala Ala Pro Pro Thr Ala Met Ala Ala Arg
                20                  25                  30

Ser Pro Arg Gly Ala Val Pro Asp Gly Ser Leu Ala Thr Thr Pro Lys
            35                  40                  45

Val Thr Met Leu Ser Ala Thr Leu Cys Tyr Thr Gly Glu Thr Cys Lys
        50                  55                  60

Tyr Ile Gly Cys Leu Thr Pro Ala Cys Ser Cys Asn Tyr Ser Asp Arg
 65                  70                  75                  80

Leu Cys Tyr Ile Ile Phe Thr Pro Val Ala
                85                  90

<210> SEQ ID NO 7
<211> LENGTH: 24
<212> TYPE: DNA
<213> ORGANISM: Artificial
<220> FEATURE:
<223> OTHER INFORMATION: oligonucleotide primer GVK27

<400> SEQUENCE: 7
gctgacagca tcgtcacctt gggc                                            24
```

<210> SEQ ID NO 8
<211> LENGTH: 25
<212> TYPE: DNA
<213> ORGANISM: Artificial
<220> FEATURE:
<223> OTHER INFORMATION: oligonucleotide primer GVK28

<400> SEQUENCE: 8
gctgcagaac cagcagtatg gccac                                              25

<210> SEQ ID NO 9
<211> LENGTH: 27
<212> TYPE: DNA
<213> ORGANISM: Artificial
<220> FEATURE:
<223> OTHER INFORMATION: oligonucleotide primer GVK29

<400> SEQUENCE: 9
catgccatgg atcggtggat atatatg                                            27

<210> SEQ ID NO 10
<211> LENGTH: 25
<212> TYPE: DNA
<213> ORGANISM: Artificial
<220> FEATURE:
<223> OTHER INFORMATION: oligonucleotide primer GVK30

<400> SEQUENCE: 10
catgccatgg atcgactatg ctctc                                              25

<210> SEQ ID NO 11
<211> LENGTH: 164
<212> TYPE: DNA
<213> ORGANISM: Artificial
<220> FEATURE:
<223> OTHER INFORMATION: cDNA of 3' end of the GL12 transcript
<220> FEATURE:
<221> NAME/KEY: misc_feature
<222> LOCATION: (45)..(45)
<223> OTHER INFORMATION: n= any nucleotide
<220> FEATURE:
<221> NAME/KEY: misc_feature
<222> LOCATION: (53)..(53)
<223> OTHER INFORMATION: n= any nucleotide
<220> FEATURE:
<221> NAME/KEY: misc_feature
<222> LOCATION: (57)..(57)
<223> OTHER INFORMATION: n= any nucleotide
<220> FEATURE:
<221> NAME/KEY: misc_feature
<222> LOCATION: (59)..(59)
<223> OTHER INFORMATION: n= any nucleotide
<220> FEATURE:
<221> NAME/KEY: misc_feature
<222> LOCATION: (61)..(61)
<223> OTHER INFORMATION: n= any nucleotide
<220> FEATURE:
<221> NAME/KEY: misc_feature
<222> LOCATION: (88)..(88)
<223> OTHER INFORMATION: n= any nucleotide
<220> FEATURE:
<221> NAME/KEY: misc_feature
<222> LOCATION: (93)..(93)
<223> OTHER INFORMATION: n= any nucleotide
<220> FEATURE:
<221> NAME/KEY: misc_feature
<222> LOCATION: (96)..(96)
<223> OTHER INFORMATION: n= any nucleotide
<220> FEATURE:
<221> NAME/KEY: misc_feature
<222> LOCATION: (126)..(126)

```
<223> OTHER INFORMATION: n= any nucleotide
<220> FEATURE:
<221> NAME/KEY: misc_feature
<222> LOCATION: (157)..(157)
<223> OTHER INFORMATION: n= any nucleotide

<400> SEQUENCE: 11
ttttacacac atccaacatg ccccccttta ttatttaatc accanaagac gtnaatntnt      60
nttattcaac accccctttt gctgcccngg tgnctnacac accactaaca catttccgtt     120
cataancatt catgctgggc cgcgctgtgc ccgacancNN aaac                      164

<210> SEQ ID NO 12
<211> LENGTH: 8514
<212> TYPE: DNA
<213> ORGANISM: Artificial
<220> FEATURE:
<223> OTHER INFORMATION: plasmid pTWV011
<220> FEATURE:
<221> NAME/KEY: misc_feature
<222> LOCATION: (52)..(1)
<223> OTHER INFORMATION: LB= left T-DNA border
<220> FEATURE:
<221> NAME/KEY: misc_feature
<222> LOCATION: (318)..(58)
<223> OTHER INFORMATION: 3' nos
<220> FEATURE:
<221> NAME/KEY: misc_feature
<222> LOCATION: (888)..(337)
<223> OTHER INFORMATION: coding region of the bar gene
<220> FEATURE:
<221> NAME/KEY: misc_feature
<222> LOCATION: (1721)..(889)
<223> OTHER INFORMATION: 35S promoter
<220> FEATURE:
<221> NAME/KEY: misc_feature
<222> LOCATION: (1991)..(1767)
<223> OTHER INFORMATION: 3' end 35S
<220> FEATURE:
<221> NAME/KEY: misc_feature
<222> LOCATION: (4511)..(2003)
<223> OTHER INFORMATION: coding region isp1a
<220> FEATURE:
<221> NAME/KEY: misc_feature
<222> LOCATION: (4546)..(4515)
<223> OTHER INFORMATION: leader sequence from the corn GL4 transcript
<220> FEATURE:
<221> NAME/KEY: misc_feature
<222> LOCATION: (5732)..(4547)
<223> OTHER INFORMATION: corn preferential promoter GL4
<220> FEATURE:
<221> NAME/KEY: misc_feature
<222> LOCATION: (5989)..(5765)
<223> OTHER INFORMATION: 3' end 35S
<220> FEATURE:
<221> NAME/KEY: misc_feature
<222> LOCATION: (7228)..(6001)
<223> OTHER INFORMATION: isp2a coding region
<220> FEATURE:
<221> NAME/KEY: misc_feature
<222> LOCATION: (7263)..(7232)
<223> OTHER INFORMATION: leader sequence of the GL4 transcript
<220> FEATURE:
<221> NAME/KEY: misc_feature
<222> LOCATION: (8449)..(7264)
<223> OTHER INFORMATION: corn root preferential promoter GL4
<220> FEATURE:
<221> NAME/KEY: misc_feature
<222> LOCATION: (8514)..(8490)
<223> OTHER INFORMATION: RB=right T-DNA border

<400> SEQUENCE: 12
cggcaggata tattcaattg taaatggctc catggcgatc gctctagagg atcttcccga      60
tctagtaaca tagatgacac cgcgcgcgat aatttatcct agtttgcgcg ctatattttg     120
```

```
ttttctatcg cgtattaaat gtataattgc gggactctaa tcataaaaac ccatctcata    180
aataacgtca tgcattacat gttaattatt acatgcttaa cgtaattcaa cagaaattat    240
atgataatca tcgcaagacc ggcaacagga ttcaatctta agaaacttta ttgccaaatg    300
tttgaacgat ctgcttcgga tcctagacgc gtgagatcag atctcggtga cgggcaggac    360
cggacgggc ggtaccggca ggctgaagtc cagctgccag aaacccacgt catgccagtt     420
cccgtgcttg aagccggccg cccgcagcat gccgcggggg catatccga gcgcctcgtg     480
catgcgcacg ctcgggtcgt tgggcagccc gatgacagcg accacgctct tgaagccctg    540
tgcctccagg gacttcagca ggtgggtgta gagcgtggag cccagtcccg tccgctggtg    600
gcgggggggag acgtacacgg tcgactcggc cgtccagtcg taggcgttgc gtgccttcca   660
ggggcccgcg taggcgatgc cggcgacctc gccgtccacc tcggcgacga gccagggata    720
gcgctcccgc agacggacga ggtcgtccgt ccactcctgc ggttcctgcg gctcggtacg    780
gaagttgacc gtgcttgtct cgatgtagtg gttgacgatg gtgcagaccg ccggcatgtc    840
cgcctcggtg gcacggcgga tgtcggccgg cgtcgttct gggtccatgg ttatagagag     900
agagatagat ttatagagag agactggtga tttcagcgtg tcctctccaa atgaaatgaa    960
cttccttata tagaggaagg gtcttgcgaa ggatagtggg attgtgcgtc atcccttacg    1020
tcagtggaga tgtcacatca atccacttgc tttgaagacg tggttggaac gtcttctttt    1080
tccacgatgc tcctcgtggg tggggtccaa tctttgggac cactgtcggc agaggcatct    1140
tgaatgatag cctttccttt atcgcaatga tggcatttgt aggagccacc ttccttttct    1200
actgtccttt cgatgaagtg acagatagct gggcaatgga atccgaggag gtttcccgaa    1260
attatccttt gttgaaaagt ctcaatagcc ctttggtctt ctgagactgt atctttgaca    1320
tttttggagt agaccagagt gtcgtgctcc accatgttga cgaagatttt cttcttgtca    1380
ttgagtcgta aaagactctg tatgaactgt tcgccagtct tcacggcgag ttctgttaga    1440
tcctcgattt gaatcttaga ctccatgcat ggccttagat tcagtaggaa ctacctttt     1500
agagactcca atctctatta cttgccttgg tttatgaagc aagccttgaa tcgtccatac    1560
tggaatagta cttctgatct tgagaaatat gtctttctct gtgttcttga tgcaattagt    1620
cctgaatctt ttgactgcat cttaacctt cttgggaagg tatttgatct cctggagatt     1680
gttactcggg tagatcgtct tgatgagacc tgctgcgtag aacgcggcc gcgtatacgt     1740
atcgatatct tcgaattcat atgcatgatc tggatttag tactggattt tggttttagg     1800
aattagaaat tttattgata gaagtatttt acaaatacaa atacatacta agggtttctt    1860
atatgctcaa cacatgagcg aaaccctata ggaaccctaa ttcccttatc tgggaactac    1920
tcacacatta ttatggagaa aatagagaga gatagatttg tagagagaga ctggtgattt    1980
cagcgtgtcc aagcttgcta gcctcagtcc acagcgaaga tcctcaccac agcggtcctg    2040
gtggagcccc acaggtcgtc cttgcaggac agggtgtaca ggaaggacct gtcggacttc    2100
acgttcttga agtccaggtt gatcctgtta gcgttcttgc cggaaccgga gtccagcacg    2160
gtcttggtct gctcaccgat caccttgtag gtgaaggaga aggtacctgg ggtctgggta    2220
atcagtgggg agtcgatgaa gtaggtagcc tcgtggtact tcacggccag tgggtcaccg    2280
aagaagtcga agtcaccctc gatgatgtcg aactgtggca ctgggtcctt gtactcgatc    2340
tcctcagcac ccacctccac gaaggacacg tcgtcccagt acacgttggt ctggccgtca    2400
cccttgatgg agatggtgtt gatctcgttg ccctccaggt ttgcaccag gatgttgatc     2460
```

```
ctctggtaac ccacgtggtc cagggtgatg ttgtcggtca cgatggactc ctgcttaccg   2520
tcgatctcga tgtccacgga caccttggag tcagccttca tgtacaggga cacgtagtag   2580
tcgatgttct tcttcagctt gttcttggac tcggtggaca gctcggtgaa agcacccttg   2640
ttagcggacc tgtactgctt cttaccggtg ttaccaccgt tcaccacgta ggtgtagtac   2700
cagttgccga tcttggtgtt gtcggactca ccaccgtcgt acaggtggag gtctttatt   2760 gtgaagttca tcttcggttc gagcttcacg tcgtacaggt tcttcacgtc cttgaaggaa   2820
ccggtggagt cgttcagctg cttcctgatc tgcttagcgg tgtactcgtc cacgtaggac   2880
tgcacggaag cctcgaagat cggctggtcg ttgtagaaca gcaggccgtc cttctcctcg   2940
atctcgtctg ggtaggccag cttcagggcc tccttcacgg ataaatttgg ggtcttgtcc   3000
tctgggttgg tgtagtcctt agcagccacc ctcttctcgg acatctggtt gccgttgtcg   3060
acgatgatgc tggcggtctt ggcggagatc tcgtcggtga tgccgttcca gtcaccagcg   3120
atggtgatgt tgccgttggt gtccttgatg gcgtacttgc cctccacctg gtcggtttcg   3180
agcaggatcg gcttcttgtt ggacaggtag gtgttcagct gctccttgtt cagtgggatc   3240
ggcctggagt tgaagtcgtc catcgtgttg atggcgatgc cgttcttgcc cttctctggg   3300
taggactggt ctggcaggat ggtcagagcg gtggtgttct ccttggcctt gatggtgccg   3360
atggtggtgc cgtccaggat gaaggaggtg gttggcttgg tctcgtagat agcaccggtg   3420
cccacgttgt tgtacctcac gttggcgttc aggtaggcgg actcagcacc gttgatgtgg   3480
gtgccgtcgt tggtggcgga gccccactcg ttggccacgg tctcggagtg ctggtagttc   3540
acggacacgc cgaaggatgg acccagaccg gaccaaccag cgttcacgtt cacgccctcg   3600
gtgttggtgt aggaccagtt ggtggactgg gaggactcca cggagtggga caggtcctcg   3660
ttcttggaca ggatcacctt ttcgagggac acgttcacgg atgggaaagc agccaccagt   3720
gggttgaagg tctccttggc gttggacagt ggcatgtccc tagcagcctt ctcgtagtcg   3780
gagtatgggt cgcccacggt gtgggcttcg agtgggttgc tggtgaactt ctggtagccc   3840
ttggaggcca gggagtcgtc ccacttcacg gccaccttgt tctggatggt gtagccgttc   3900
tcctcccaca cgtccgggat ggagtcgccg tcggtgtcgg tgtcctcgtc gatgtccctc   3960
ttggtcttct gggtgaacag gttggtcttg gaggccttct tcaggaacac ctgggtctcc   4020
ttcttgttga actctgggtt cctcagctcg tcctgctgca cctgctggga gtggttctgg   4080
gagtcgatct tgaacagctt cagctccttg aagatcttgt tgtcgatgtg cagggcgtcg   4140
tcggactggt actcgatctt gatctgcacc agctggccct tttcgaggtg cacggactgc   4200
ttgttgttgc cctttctcgga gatcaccttg ccgtccagct cgatgatggc gttctcgtcg   4260
tcggacagct tgaaggtgaa gtcaccagtg gcggaggact ggatcaggcc gatccagcgg   4320
atggagtggt actcctggtg cttctggtcc acgagggtgt tagcggtctg ctggtcgtag   4380
atcagggtgt tgtccctggt tggagcgaac agggtcaggt cgttgaagtc cttgcccttg   4440
aagtagtagc ccagcaggcc ctccctgtcg atctggttgt ccttcgaagc ctgggtggtg   4500
gtggcgatag ccatggatcg gtggatatat atgctctctc tccttggttc cagcagcctc   4560
accgatcccg gccattttat aggcagtcat aagcaactgt gtagcacatc tgcgaggtag   4620
aaacaggtaa tacactgtgt agcacatctg aggtagaaac agctgtggca gatggatcac   4680
aactggctgt attttaagct gcatgaggtt cacgttgtgg aacccacttg ggttggatcg   4740
cgcgctgaag cccaatcacc tcttccaact gctatttccg ctcggtgtca tcaagacaga   4800
gagagattca gagattctag agaacaacag tgctcaagga aaacaaccca tacccgctcg   4860
```

```
ttaactgtcg tgttatctgt agtagtaaat tcaggccgcg cacgtcgacg gttaactgtt    4920
gtgttatcct ctttagttta gtttgctacc taacttgtca tactttgttt aattttttgt    4980
atctaaggtt agttctttaa tttggatgac taattttaga taaagtgtga cacagttagc    5040
ggaatagtac tatccggatt ttttttttg gcgccagtcc gggcaacaaa tacaactggg     5100
ctctggcccc cctatataca acaaaattgg ctttcaccaa acaacacgtc agcccagaca    5160
catatttcat tggcgtcatt ttctttacac attataaaat tgaaacaaaa agactcacac    5220
ttcagctgct tctgtcactc tacttcagaa aaaaaaatca tctattttc ttgatgcctg     5280 tttgatatat aggtgtttat atatatagag agagataatg agtccctctc atcaagatat    5340
ccatatcata atggtacggt attttatgga taaaaaagta catcgtacgt atcacaaatc    5400
tacaataata gaatggccat ctctgaaaac agtttgattt aggtgcggtc tggtacaaca    5460
acgtcatagt attttccat cagacaagta gatcaacatt tcatgcataa ggaatacgat     5520
gggtaaaata tatttcattt tagactaaat atacatttat taattaaccct atgaatatag   5580 tttgtatgta tatctatatt tattatcatt caaatgagtg tggacggaaa aaaagaggct    5640
agaaagaact atatttcaaa ctgagggagt ataaaagaca caaatttata caagtttcaa    5700
gtataaagta cactcgtccc agtgcagaaa gccgggatcc ccgggctagg cgcgccatat    5760
gcatgatctg gattttagta ctggattttg gttttaggaa ttagaaattt tattgataga    5820 agtatttttac aaatacaaat acatactaag ggtttcttat atgctcaaca catgagcgaa   5880
accctatagg aaccctaatt cccttatctg ggaactactc acacattatt atggagaaaa    5940
tagagagaga tagatttgta gagagagact ggtgatttca gcgtgtccaa gcttgctagc    6000
ctcacttggt cagcagggta gcgtccacta cgtacctctt cacacccttg atcaccacct    6060
cggtgatctt gtcgatgtgg tagttggagt ccttgtcgat caggatctcc ttctcggaag    6120
cgaagccacc gatagcggac aggtaggcac cagtggaacc ctttggcacc tgcagcctca    6180
ggatgaactt cctggagccg aaagcggaca gcctctcgga ggacagggag gtggacatgt    6240
aacccttgtc ctccttcatg gtgttcagga acttctcctc catctccttc agggatggca    6300
gtgggtcgga atctggtaa ccgaactcgg ccataccgca ccacctgtac acggtgatgt     6360
tctctgggat cggctgcttc tccagagcct cggagatgtt cttgatctgg gtgtccagct    6420
tctcgttgcc ggagccaccc tggttccgca ggtagtcgtt gatctgcttg tagtcctgcc    6480
tagcgtagcc gtccagggcc tccctctgtg ggtcggtcag gttcttagcc caaccctcgt    6540
agttcttcat gccccacctg tgagcctcgg cgttgatgtc gttcttgaag tccagggact    6600
tcttcagggt accctggatc tgcaggcact cgtaacccct cttcaccacc ttggagatgt     6660
tgtccacgtg cagcacgtag ccgttgtcga tcagcatctt gtactcgttg ttgttcagga    6720
tcacaccagc cttggtcggg atggtggagc ccttgccgga tggcacggtc acttggagga    6780
tgatcctctc cttggaggac acgttctgag cagtcaggtg ggtgtccagg taggagtcga    6840
acttgatgtc cttgcccagg aactgctcct tgaactgggc ctgcacgtcg tgttgatgg     6900 tgttgccctc ggtcagtggc ttgttaaatc cgatggtgga tggctccacg ttcttgtagg    6960
tcacgatgga ggaggacagg ttggccttgt cgaacatctt gtcgatctcc ttcaggtcct    7020
tgatctcgtc ctcgaaggag ccagccatgc tgaaggtgat ctccttgtag ttcttcttga    7080
tgtcgttctt gttgtccagg aaattattca tacgcgtctt ctcggtcacg gtcagcttcc    7140
actccttctc cttctccttg ccccactcct tggccttctc cttgtcctcc ttgaagtcct    7200
```

```
cggtgttgtt ggtggtcttc actagtgcca tggatcggtg gatatatatg ctctctctcc   7260
ttggttccag cagcctcacc gatcccggcc attttatagg cagtcataag caactgtgta   7320
gcacatctgc gaggtagaaa caggtaatac actgtgtagc acatctgagg tagaaacagc   7380
tgtggcagat ggatcacaac tggctgtatt ttaagctgca tgaggttcac gttgtggaac   7440
ccacttgggt tggatcgcgc gctgaagccc aatcacctct tccaactgct atttccgctc   7500
ggtgtcatca agacagagag agattcagag attctagaga caacagtgc tcaaggaaaa    7560 caacccatac ccgctcgtta actgtcgtgt tatctgtagt agtaaattca ggccgcgcac   7620
gtcgacggtt aactgttgtg ttatcctctt tagtttagtt tgctacctaa cttgtcatac   7680
tttgtttaat tttttgtatc taaggttagt tctttaattt ggatgactaa ttttagataa   7740
agtgtgacac agttagcgga atagtactat ccggattttt ttttttggcg ccagtccggg   7800
caacaaatac aactgggctc tggccccct atatacaaca aaattggctt tcaccaaaca    7860
acacgtcagc ccagacacat atttcattgg cgtcattttc tttacacatt ataaaattga   7920
aacaaaaaga ctcacacttc agctgcttct gtcactctac ttcagaaaaa aaatcatct    7980 attttcttg atgcctgttt gatatatagg tgtttatata tatagagaga gataatgagt    8040
ccctctcatc aagatatcca tatcataatg gtacggtatt ttatggataa aaaagtacat   8100
cgtacgtatc acaaatctac aataatagaa tggccatctc tgaaaacagt ttgatttagg   8160
tgcggtctgg tacaacaacg tcatagtatt tttccatcag acaagtagat caacatttca   8220
tgcataagga atacgatggg taaaatatat ttcattttag actaaatata catttattaa   8280
ttaacctatg aatatagttt gtatgtatat ctatatttat tatcattcaa atgagtgtgg   8340
acggaaaaaa agaggctaga aagaactata tttcaaactg agggagtata aaagacacaa   8400
atttatacaa gtttcaagta taaagtacac tacgtccagt gcagaaagcc gggatccccg   8460
ggcaggcctg caggtcgacg gccgagtact ggcaggatat accgttgt aatt            8514
```

<210> SEQ ID NO 13
<211> LENGTH: 8692
<212> TYPE: DNA
<213> ORGANISM: Artificial
<220> FEATURE:
<223> OTHER INFORMATION: plasmid pTW018 T-DNA sequence
<220> FEATURE:
<221> NAME/KEY: misc_feature
<222> LOCATION: (25)..(1)
<223> OTHER INFORMATION: LB= left border region (complement)
<220> FEATURE:
<221> NAME/KEY: misc_feature
<222> LOCATION: (318)..(58)
<223> OTHER INFORMATION: 3' nos (complement)
<220> FEATURE:
<221> NAME/KEY: misc_feature
<222> LOCATION: (888)..(337)
<223> OTHER INFORMATION: coding region of the bar gene (complement)
<220> FEATURE:
<221> NAME/KEY: misc_feature
<222> LOCATION: (1721)..(889)
<223> OTHER INFORMATION: 35S promoter (complement)
<220> FEATURE:
<221> NAME/KEY: misc_feature
<222> LOCATION: (1991)..(1767)
<223> OTHER INFORMATION: 3' 35S (complement)
<220> FEATURE:
<221> NAME/KEY: misc_feature
<222> LOCATION: (4511)..(2003)
<223> OTHER INFORMATION: coding region isp1a (complement)
<220> FEATURE:
<221> NAME/KEY: misc_feature
<222> LOCATION: (4542)..(4518)
<223> OTHER INFORMATION: leader sequence from the corn GL5 transcript

```
                            (complement)
<220> FEATURE:
<221> NAME/KEY: misc_feature
<222> LOCATION: (5822)..(4543)
<223> OTHER INFORMATION: GL5 promoter (complement)
<220> FEATURE:
<221> NAME/KEY: misc_feature
<222> LOCATION: (6078)..(5854)
<223> OTHER INFORMATION: 3' 35S (complement)
<220> FEATURE:
<221> NAME/KEY: misc_feature
<222> LOCATION: (7317)..(6090)
<223> OTHER INFORMATION: isp2a coding region (complement)
<220> FEATURE:
<221> NAME/KEY: misc_feature
<222> LOCATION: (7348)..(7324)
<223> OTHER INFORMATION: leader sequence of the corn GL5 transcript
                        (complement)
<220> FEATURE:
<221> NAME/KEY: misc_feature
<222> LOCATION: (8628)..(7349)
<223> OTHER INFORMATION: promoter of the corn GL5 transcript
                        (complement)
<220> FEATURE:
<221> NAME/KEY: misc_feature
<222> LOCATION: (8692)..(8668)
<223> OTHER INFORMATION: Right T-DNA border (complement)
<220> FEATURE:
<221> NAME/KEY: misc_feature
<222> LOCATION: (5630)..(5630)
<223> OTHER INFORMATION: n=any nucleotide
<220> FEATURE:
<221> NAME/KEY: misc_feature
<222> LOCATION: (8436)..(8436)
<223> OTHER INFORMATION: n=any nucleotide

<400> SEQUENCE: 13
cggcaggata tattcaattg taaatggctc catggcgatc gctctagagg atcttcccga      60
tctagtaaca tagatgacac cgcgcgcgat aatttatcct agtttgcgcg ctatattttg     120
ttttctatcg cgtattaaat gtataattgc gggactctaa tcataaaaac ccatctcata     180
aataacgtca tgcattacat gttaattatt acatgcttaa cgtaattcaa cagaaattat     240
atgataatca tcgcaagacc ggcaacagga ttcaatctta agaaacttta ttgccaaatg     300
tttgaacgat ctgcttcgga tcctagacgc gtgagatcag atctcggtga cgggcaggac     360 cggacgggc ggtaccggca ggctgaagtc cagctgccag aaacccacgt catgccagtt     420
cccgtgcttg aagccggccg cccgcagcat gccgcggggg gcatatccga gcgcctcgtg     480
catgcgcacg ctcgggtcgt tgggcagccc gatgacagcg accacgctct tgaagccctg     540
tgcctccagg gacttcagca ggtgggtgta gagcgtggag cccagtcccg tccgctggtg     600 gcgggggggag acgtacacgg tcgactcggc cgtccagtcg taggcgttgc gtgccttcca     660
ggggcccgcg taggcgatgc cggcgacctc gccgtccacc tcggcgacga gccagggata     720
gcgctcccgc agacggacga ggtcgtccgt ccactcctgc ggttcctgcg gctcggtacg     780
gaagttgacc gtgcttgtct cgatgtagtg gttgacgatg gtgcagaccg ccggcatgtc     840
cgcctcggtg gcacggcgga tgtcggccgg gcgtcgttct gggtccatgg ttatagagag     900
agagatagat ttatagagag agactggtga tttcagcgtg tcctctccaa atgaaatgaa     960
cttccttata tagaggaagg gtcttgcgaa ggatagtggg attgtgcgtc atcccttacg    1020
tcagtggaga tgtcacatca atccacttgc tttgaagacg tggttggaac gtcttctttt    1080
tccacgatgc tcctcgtggg tgggggtcca tctttgggac cactgtcggc agaggcatct    1140
tgaatgatag cctttccttt atcgcaatga tggcatttgt aggagccacc ttccttttct    1200
actgtccttt cgatgaagtg acagatagct gggcaatgga atccgaggag gtttcccgaa    1260
```

```
attatccttt gttgaaaagt ctcaatagcc ctttggtctt ctgagactgt atctttgaca    1320
tttttggagt agaccagagt gtcgtgctcc accatgttga cgaagatttt cttcttgtca    1380
ttgagtcgta aaagactctg tatgaactgt tcgccagtct tcacggcgag ttctgttaga    1440
tcctcgattt gaatcttaga ctccatgcat ggccttagat tcagtaggaa ctacctttt     1500 agagactcca atctctatta cttgccttgg tttatgaagc aagccttgaa tcgtccatac    1560
tggaatagta cttctgatct tgagaaatat gtctttctct gtgttcttga tgcaattagt    1620
cctgaatctt ttgactgcat ctttaacctt cttgggaagg tatttgatct cctggagatt    1680
gttactcggg tagatcgtct tgatgagacc tgctgcgtag gaacgcggcc gcgtatacgt    1740
atcgatatct tcgaattcat atgcatgatc tggattttag tactggattt tggttttagg    1800
aattagaaat tttattgata gaagtatttt acaaatacaa atacatacta agggtttctt    1860
atatgctcaa cacatgagcg aaaccctata ggaaccctaa ttcccttatc tgggaactac    1920
tcacacatta ttatggagaa aatagagaga gatagatttg tagagagaga ctggtgattt    1980
cagcgtgtcc aagcttgcta gcctcagtcc acagcgaaga tcctcaccac agcggtcctg    2040
gtggagcccc acaggtcgtc cttgcaggac agggtgtaca ggaaggacct gtcggacttc    2100
acgttcttga agtccaggtt gatcctgtta gcgttcttgc cggaaccgga gtccagcacg    2160
gtcttggtct gctcaccgat caccttgtag gtgaaggaga aggtacctgg ggtctgggta    2220
atcagtgggg agtcgatgaa gtaggtagcg tcgtggtact tcacggccag tgggtcaccg    2280
aagaagtcga agtcaccctc gatgatgtcg aactgtggca ctgggtcctt gtactcgatc    2340
tcctcagcac ccacctccac gaaggacacg tcgtcccagt acacgttggt ctggccgtca    2400
cccttgatgg agatggtgtt gatctcgttg ccctccaggt ttggcaccag gatgttgatc    2460
ctctggtaac ccacgtggtc cagggtgatg ttgtcggtca cgatggactc ctgcttaccg    2520
tcgatctcga tgtccacgga caccttggag tcagccttca tgtacaggga cacgtagtag    2580
tcgatgttct tcttcagctt gttcttggac tcggtggaca gctcggtgaa agcacccttg    2640
ttagcggacc tgtactgctt cttaccggtg ttaccaccgt tcaccacgta ggtgtagtac    2700
cagttgccga tcttggtgtt gtcggactca ccaccgtcgt acagggtgga ggtctttatt    2760
gtgaagttca tcttcggttc gagcttcacg tcgtacaggt tcttcacgtc cttgaaggaa    2820
ccggtggagt cgttcagctg cttcctgatc tgcttagcgg tgtactcgtc cacgtaggac    2880
tgcacggaag cctcgaagat cggctggtcg ttgtagaaca gcaggccgtc cttctcctcg    2940
atctcgtctg ggtaggccag cttcagggcc tccttcacgg ataaatttgg ggtcttgtcc    3000
tctgggttgg tgtagtcctt agcagccacc ctcttctcgg acatctggtt gccgttgtcg    3060
acgatgatgc tggcggtctt ggcggagatc tcgtcggtga tgccgttcca gtcaccagcg    3120
atggtgatgt tgccgttggt gtccttgatg gcgtacttgc cctccacctg gtcggtttcg    3180
agcaggatcg gcttcttgtt ggacaggtag gtgttcagct gctccttgtt cagtgggatc    3240
ggcctggagt tgaagtcgtc catcgtgttg atgcgatgc cgttcttgcc cttctctggg    3300
taggactggt ctggcaggat ggtcagagcg gtggtgttct ccttggcctt gatggtgccg    3360
atggtggtgc cgtccaggat gaaggaggtg gttggcttgg tctcgtagat agcaccggtg    3420
cccacgttgt tgtacctcac gttggcgttc aggtaggcgg actcagcacc gttgatgtgg    3480
gtgccgtcgt tggtggcgga gccccactcg ttggccacgg tctcggagtg ctggtagttc    3540
acggacacgc cgaaggatgg acccagaccg gaccaaccag cgttcacgtt cacgccctcg    3600
```

```
gtgttggtgt aggaccagtt ggtggactgg gaggactcca cggagtggga caggtcctcg   3660
ttcttggaca ggatcacctt ttcgagggac acgttcacgg atgggaaagc agccaccagt   3720
gggttgaagg tctccttggc gttggacagt ggcatgtccc tagcagcctt ctcgtagtcg   3780
gagtatgggt cgcccacggt gtgggcttcg agtgggttgc tggtgaactt ctggtagccc   3840
ttggaggcca gggagtcgtc ccacttcacg gccaccttgt tctggatggt gtagccgttc   3900
tcctcccaca cgtccgggat ggagtcgccg tcggtgtcgg tgtcctcgtc gatgtccctc   3960
ttggtcttct gggtgaacag gttggtcttg gaggccttct tcaggaacac ctgggtctcc   4020
ttcttgttga actctgggtt cctcagctcg tcctgctgca cctgctggga gtggttctgg   4080
gagtcgatct tgaacagctt cagctccttg aagatcttgt tgtcgatgtg cagggcgtcg   4140
tcggactggt actcgatctt gatctgcacc agctggccct tttcgaggtg cacggactgc   4200
ttgttgttgc ccttctcgga gatcaccttg ccgtccagct cgatgatggc gttctcgtcg   4260
tcggacagct tgaaggtgaa gtcaccagtg gcggaggact ggatcaggcc gatccagcgg   4320
atggagtggt actcctggtg cttctggtcc acgagggtgt tagcggtctg ctggtcgtag   4380
atcagggtgt tgtccctggt tggagcgaac agggtcaggt cgttgaagtc cttgcccttg   4440
aagtagtagc ccagcaggcc ctccctgtcg atctggttgt ccttcgaagc ctgggtggtg   4500
gtggcgatag ccatggatcg actatgctct ctatctgatt ggtttggctt tgctccagca   4560
gccagccatt ttataggcag cagtcactaa actgtaggct gtagcacgtc tgacagacag   4620
gtagatggat cacaactggc tgtattttaa aaagctgcac gaggttcacg ttgtgtcgtc   4680
gtggtataga taaatgtgca tgcagcaatg gaacaatatt ggggttgatg actgaatcgc   4740
tcaagctagc tagcccaatc atctcttcca actgctaccc gctgtgtctc ataaacacgc   4800
aggtccagcg attctaaacc gcaacagtgc tcaacgaaaa ctacccttac ccgctggtta   4860
attattgtgt tatcatattt aaatgctgtc attttcttta caaattataa aacttgggac   4920
gtgtttggtt cgctgcctat acttatttta tgtattggat tctatgcgca aagagcaaaa   4980
ttccagtacc aaatgtttgt tgtattttat tgggtagcgt gtacgtcgca cattctgtaa   5040
tacaacctcc gttcacagat atatgacatg ttgatttttt taaaaaactt tgaccattta   5100
tcttattcaa aagtataaaa ttttaattaa gcacaaacta ccttaagtga taaaacaaac   5160
cacacaaaaa ataaatgaca actccattat ttttaaataa gacaagtgat taaagttttt   5220
taaaaagtca gcgatgtcat atatttatga acggtatata tatatatata taacacccc   5280 atatcgagca ggcatcaaga aaaacatatc gatgattttt gttttcctaa agtagagtga   5340
caagctaaac aaatgacata ttttttgtttc agttttgtaa ggccattctc agtggtgagc   5400
ttcagaacat gtgacatatt ttttttgttt tagttttgta aggccttttct cagtggtgag   5460 ctttagaaca agtgacatct ttttgtttca gttttgtaag gtcattctta gtggtgagct   5520
tcagaacaag tgagatgaga tcttttttgtt tcagttttgt taggccagtt tcatcggtga   5580
gcttcacaac aagtgacatc ttcttttcag ttttgtaagg ccatttttcan cggtgagctt   5640 cggtacaatg ttttccatgt tgtcacacca tatttaaact aggtaattgt atatatagaa   5700
ttttatctct atgaaactct accatctccc ataagctctt tctatatctc tgcttttaat   5760
tgtatgtcat gtcactatgt atgatggtgt atcatcgtat ataatgagta tgaaattccg   5820
ccaatcacta ggggctaggc gcgccatatg catgatctgg attttagtac tggattttgg   5880
ttttaggaat tagaaatttt attgatagaa gtattttaca aatacaaata catactaagg   5940
gtttcttata tgctcaacac atgagcgaaa ccctatagga accctaattc ccttatctgg   6000
```

-continued

```
gaactactca cacattatta tggagaaaat agagagagat agatttgtag agagagactg    6060
gtgatttcag cgtgtccaag cttgctagcc tcacttggtc agcagggtag cgtccactac    6120
gtacctcttc acaccttga tcaccacctc ggtgatcttg tcgatgtggt agttggagtc    6180
cttgtcgatc aggatctcct tctcggaagc gaagccaccg atagcggaca ggtaggcacc    6240
agtggaaccc tttggcacct gcagcctcag gatgaacttc ctggagccga aagcggacag    6300
cctctcggag gacagggagg tggacatgta acccttgtcc tccttcatgg tgttcaggaa    6360
cttctcctcc atctccttca gggatggcag tgggtcggaa atctggtaac cgaactcggc    6420
cataccgcac cacctgtaca cggtgatgtt ctctgggatc ggctgcttct ccagagcctc    6480
ggagatgttc ttgatctggg tgtccagctt ctcgttgccg gagccaccct ggttccgcag    6540
gtagtcgttg atctgcttgt agtcctgcct agcgtagccg tccagggcct ccctctgtgg    6600
gtcggtcagg ttcttagccc aaccctcgta gttcttcatg ccccacctgt gagcctcggc    6660
gttgatgtcg ttcttgaagt ccagggactt cttcagggta ccctggatct gcaggcactc    6720 gtaaccctt ttcaccacct ggagatgtt gtccacgtgc agcacgtagc cgttgtcgat     6780
cagcatcttg tactcgttgt tgttcaggat cacaccagcc ttggtcggga tggtggagcc    6840
cttgccggat ggcacggtca cttggaggat gatcctctcc ttggaggaca cgttctgagc    6900
agtcaggtgg gtgtccaggt aggagtcgaa cttgatgtcc ttgcccagga actgctcctt    6960
gaactgggcc tgcacgtcgg tgttgatggt gttgccctcg gtcagtggct tgttaaatcc    7020
gatggtggat ggctccacgt tcttgtaggt cacgatggag gaggacaggt tggccttgtc    7080
gaacatcttg tcgatctcct tcaggtcctt gatctcgtcc tcgaaggagc cagccatgct    7140
gaaggtgatc tccttgtagt tcttcttgat gtcgttcttg ttgtccagga aattattcat    7200
acgcgtcttc tcggtcacgg tcagcttcca ctccttctcc ttctccttgc cccactcctt    7260
ggccttctcc ttgtcctcct tgaagtcctc ggtgttgttg gtggtcttca ctagtgccat    7320
ggatcgacta tgctctctat ctgattggtt tggctttgct ccagcagcca gccattttat    7380
aggcagcagt cactaaactg taggctgtag cacgtctgac agacaggtag atggatcaca    7440
actggctgta ttttaaaaag ctgcacgagg ttcacgttgt gtcgtcgtgg tatagataaa    7500
tgtgcatgca gcaatggaac aatattgggg ttgatgactg aatcgctcaa gctagctagc    7560
ccaatcatct cttccaactg ctacccgctg tgtctcataa acacgcaggt ccagcgattc    7620
taaaccgcaa cagtgctcaa cgaaaactac ccttacccgc tggttaatta ttgtgttatc    7680
atatttaaat gctgtcattt tctttacaaa ttataaaact tgggacgtgt ttggttcgct    7740
gcctatactt attttatgta ttggattcta tgcgcaaaga gcaaaattcc agtaccaaat    7800
gtttgttgta ttttattggg tagcgtgtac gtcgcacatt ctgtaataca acctccgttc    7860
acagatatat gacatgttga ttttttttaaa aactttgac catttatctt attcaaaagt    7920
ataaaatttt aattaagcac aaactacctt aagtgataaa acaaaccaca caaaaaataa    7980
atgacaactc attattttt aaataagaca agtgattaaa gttttttaaa aagtcagcga    8040
tgtcatatat ttatgaacgg tatatatata tatatatata acacccatat cgagcaggca    8100
tcaagaaaaa catatcgatg attttttgttt tcctaaagta gagtgacaag ctaaacaaat    8160
gacatatttt tgtttcagtt ttgtaaggcc attctcagtg gtgagcttca gaacatgtga    8220
catatttttt ttgttttagt tttgtaaggc ctttctcagt ggtgagcttt agaacaagtg    8280 acatctttttt gtttcagttt tgtaaggtca ttcttagtgg tgagcttcag aacaagtgag    8340
```

```
atgagatctt tttgtttcag ttttgttagg ccagtttcat cggtgagctt cacaacaagt      8400
gacatcttct tttcagtttt gtaaggccat tttcancggt gagcttcggt acaatgtttt      8460
ccatgttgtc acaccatatt taaactaggt aattgtatat atagaatttt atctctatga      8520
aactctacca tctcccataa gctctttcta tatctctgct tttaattgta tgtcatgtca      8580
ctatgtatga tggtgtatca tcgtatataa tgagtatgaa attccgccaa tcactagggg      8640
caggcctgca ggtcgacggc cgagtactgg caggatatat accgttgtaa tt              8692
```

<210> SEQ ID NO 14
<211> LENGTH: 500
<212> TYPE: DNA
<213> ORGANISM: Zea mays
<220> FEATURE:
<221> NAME/KEY: misc_feature
<222> LOCATION: (127)..(127)
<223> OTHER INFORMATION: n=any nucleotide
<220> FEATURE:
<221> NAME/KEY: misc_feature
<222> LOCATION: (131)..(131)
<223> OTHER INFORMATION: n=any nucleotide
<220> FEATURE:
<221> NAME/KEY: misc_feature
<222> LOCATION: (156)..(156)
<223> OTHER INFORMATION: n=any nucleotide
<220> FEATURE:
<221> NAME/KEY: misc_feature
<222> LOCATION: (193)..(193)
<223> OTHER INFORMATION: n=any nucleotide
<220> FEATURE:
<221> NAME/KEY: misc_feature
<222> LOCATION: (289)..(289)
<223> OTHER INFORMATION: n=any nucleotide
<220> FEATURE:
<221> NAME/KEY: misc_feature
<222> LOCATION: (463)..(463)
<223> OTHER INFORMATION: n=any nucleotide
<220> FEATURE:
<221> NAME/KEY: misc_feature
<222> LOCATION: (486)..(486)
<223> OTHER INFORMATION: n=any nucleotide

<400> SEQUENCE: 14

```
ggcggaattt catactcatt atatacgatg ataccatc atacatagtg acatgacata         60
caattaaaag cagagatata gaaagagctt atgggagatg gtagagtttc atagagataa      120
aattctntat ntacaattac ctagtttaaa tatggngtga caacatggaa aacattgtac      180
cgaagctcac cgntgaaaat ggccttacaa aactgaaaag aagatgtcac ttgttgtgaa      240
gctcaccgat gaaactggcc taacaaaact gaaacaaaaa gatctcatnt cacttgttct      300
gaagctcacc actaagaatg accttacaaa actgaaacaa aaaagatgtc cttgttctaa      360
agctcaccac tgagaaaggc cttacaaaac taaaacaaaa aaaatttgtc acatgtcttg      420
aagctcacca ctgagaatgg ccttacaaaa ctgaacaaaa atntgtcatt ggtttagct        480 ttgtcnctct actttaagga                                                  500
```

<210> SEQ ID NO 15
<211> LENGTH: 604
<212> TYPE: DNA
<213> ORGANISM: Zea mays

<400> SEQUENCE: 15

```
tgaataagat aaatggtcaa agttttttaa aaaaatcaaa catgtcatat atctgtgaac       60
ggaggttgta ttcagaatg tgcgacgtac acgctaccca ataaaataca acaaacattt      120
ggtactggaa ttttgctctt tgcgcataga atccaataca taaaataagt ataggcagcg      180
```

```
aaccaaacac gtcccaagtt ttataatttg taaagaaaat gacagcattt aaatatgata    240
acacaataat taaccagcgg gtaagggtag ttttcgttga gcactgttgc ggtttagaat    300
cgctggacct gcgtgtttat gagacacagc gggtagcagt tggaagagat gattgggcta    360
gctagcttga gcgattcagt catcaacccc aatattgttc cattgctgca tgcacattta    420
tctataccac gacgacacaa cgtgaacctc gtgcagcttt ttaaaataca gccagttgtg    480
atccatctac ctgtctgtca gacgtgctac agcctacagt ttagtgactg ctgcctataa    540
aatggctggc tgctggagca aagccaaacc aatcagatag agagcatagt cgatccatgg    600
catg                                                                  604

<210> SEQ ID NO 16
<211> LENGTH: 25
<212> TYPE: DNA
<213> ORGANISM: Artificial
<220> FEATURE:
<223> OTHER INFORMATION: oligonucleotide primer GVK22

<400> SEQUENCE: 16
gctgtgtgag agtagtagtg gcttc                                            25

<210> SEQ ID NO 17
<211> LENGTH: 24
<212> TYPE: DNA
<213> ORGANISM: Artificial
<220> FEATURE:
<223> OTHER INFORMATION: oligonucleotide primer GVK23

<400> SEQUENCE: 17
cacaagcgtg gctgacagca tcgt                                             24

<210> SEQ ID NO 18
<211> LENGTH: 26
<212> TYPE: DNA
<213> ORGANISM: Artificial
<220> FEATURE:
<223> OTHER INFORMATION: oligonucleotide primer GVK24

<400> SEQUENCE: 18
gctcacgaga ggcagcgcgc gtcgtc                                           26

<210> SEQ ID NO 19
<211> LENGTH: 21
<212> TYPE: DNA
<213> ORGANISM: Artificial
<220> FEATURE:
<223> OTHER INFORMATION: oligonucleotide primer GVK25

<400> SEQUENCE: 19
gtaaaagttg tggcttcccg g                                                21

<210> SEQ ID NO 20
<211> LENGTH: 25
<212> TYPE: DNA
<213> ORGANISM: Artificial
<220> FEATURE:
<223> OTHER INFORMATION: oligonucleotide primer GVK26

<400> SEQUENCE: 20
ccgcgctgtg cccgacagct taaac                                            25

<210> SEQ ID NO 21
```

```
<211> LENGTH: 27
<212> TYPE: DNA
<213> ORGANISM: Artificial
<220> FEATURE:
<223> OTHER INFORMATION: oligonucleotide primer GVK31

<400> SEQUENCE: 21
gggttggatc gcgccaatca cctcttc                                        27

<210> SEQ ID NO 22
<211> LENGTH: 24
<212> TYPE: DNA
<213> ORGANISM: Artificial
<220> FEATURE:
<223> OTHER INFORMATION: oligonucleotide primer GVK32

<400> SEQUENCE: 22
ccgctcggtg tcatcaagac agag                                           24

<210> SEQ ID NO 23
<211> LENGTH: 26
<212> TYPE: DNA
<213> ORGANISM: Artificial
<220> FEATURE:
<223> OTHER INFORMATION: oligonucleotide primer GVK33

<400> SEQUENCE: 23
gctcaaggaa aacaacccat acccgc                                         26

<210> SEQ ID NO 24
<211> LENGTH: 24
<212> TYPE: DNA
<213> ORGANISM: Artificial
<220> FEATURE:
<223> OTHER INFORMATION: oligonucleotide primer GVK38

<400> SEQUENCE: 24
ggcgccagtc cgggcaacaa atac                                           24

<210> SEQ ID NO 25
<211> LENGTH: 25
<212> TYPE: DNA
<213> ORGANISM: Artificial
<220> FEATURE:
<223> OTHER INFORMATION: oligonucleotide primer GVK39

<400> SEQUENCE: 25
gggctctggc cccctatat acaac                                           25

<210> SEQ ID NO 26
<211> LENGTH: 27
<212> TYPE: DNA
<213> ORGANISM: Artificial
<220> FEATURE:
<223> OTHER INFORMATION: oligonucleotide primer GVK45

<400> SEQUENCE: 26
cgggatcccg gctttctgca ctggacg                                        27

<210> SEQ ID NO 27
<211> LENGTH: 15
<212> TYPE: DNA
<213> ORGANISM: Artificial
<220> FEATURE:
<223> OTHER INFORMATION: oligonucleotide primer MDB285
<220> FEATURE:
<221> NAME/KEY: misc_feature
```

```
<222> LOCATION: (1)..(1)
<223> OTHER INFORMATION: n=any nucleotide

<400> SEQUENCE: 27
ntcgastwts gwgtt                                                    15

<210> SEQ ID NO 28
<211> LENGTH: 16
<212> TYPE: DNA
<213> ORGANISM: Artificial
<220> FEATURE:
<223> OTHER INFORMATION: oligonucleotide primer MDB286
<220> FEATURE:
<221> NAME/KEY: misc_feature
<222> LOCATION: (1)..(1)
<223> OTHER INFORMATION: n=any nucleotide
<220> FEATURE:
<221> NAME/KEY: misc_feature
<222> LOCATION: (11)..(11)
<223> OTHER INFORMATION: n=any nucleotide

<400> SEQUENCE: 28
ngtcgaswga nawgaa                                                   16

<210> SEQ ID NO 29
<211> LENGTH: 16
<212> TYPE: DNA
<213> ORGANISM: Artificial
<220> FEATURE:
<223> OTHER INFORMATION: oligonucleotide primer MDB363
<220> FEATURE:
<221> NAME/KEY: misc_feature
<222> LOCATION: (5)..(5)
<223> OTHER INFORMATION: n=any nucleotide
<220> FEATURE:
<221> NAME/KEY: misc_feature
<222> LOCATION: (10)..(10)
<223> OTHER INFORMATION: n=any nucleotide

<400> SEQUENCE: 29
csggntgawn taawac                                                   16

<210> SEQ ID NO 30
<211> LENGTH: 15
<212> TYPE: DNA
<213> ORGANISM: Artificial
<220> FEATURE:
<223> OTHER INFORMATION: oligonucleotide primer MDB364
<220> FEATURE:
<221> NAME/KEY: misc_feature
<222> LOCATION: (5)..(5)
<223> OTHER INFORMATION: n=any nucleotide

<400> SEQUENCE: 30
sscgnaawtt catwc                                                    15

<210> SEQ ID NO 31
<211> LENGTH: 15
<212> TYPE: DNA
<213> ORGANISM: Artificial
<220> FEATURE:
<223> OTHER INFORMATION: oligonucleotide primer MDB552
<220> FEATURE:
<221> NAME/KEY: misc_feature
<222> LOCATION: (1)..(1)
<223> OTHER INFORMATION: n=any nucleotide

<400> SEQUENCE: 31
ngtcsagwaw scatt                                                    15
```

```
<210> SEQ ID NO 32
<211> LENGTH: 16
<212> TYPE: DNA
<213> ORGANISM: Artificial
<220> FEATURE:
<223> OTHER INFORMATION: oligonucleotide primer MDB556
<220> FEATURE:
<221> NAME/KEY: misc_feature
<222> LOCATION: (2)..(2)
<223> OTHER INFORMATION: n=any nucleotide
<220> FEATURE:
<221> NAME/KEY: misc_feature
<222> LOCATION: (6)..(6)
<223> OTHER INFORMATION: n=any nucleotide

<400> SEQUENCE: 32
cngasnagwt wgcata                                              16
```

CORN ROOT PREFERENTIAL PROMOTERS AND USES THEREOF

This application is a continuation-in-part of application Ser. No. 60/1399,383, filed on Jul. 31, 2002, the entire contents of which are hereby incorporated by reference.

FIELD OF THE INVENTION

The invention relates to the isolation of promoters from corn capable of directing transcription of an operably linked foreign DNA sequence preferentially, selectively or exclusively in the roots of plants, such as corn plants. The invention also relates to the use of chimeric genes for the preferential or selective expression of biologically active RNA of interest in the roots of plants, such as corn plants. Plants, such as corn plants, comprising corn root preferential or selective promoters operably linked to a foreign DNA sequence which, upon transcription, yield biologically active RNA preferentially or selectively in the roots of plants are also provided.

DESCRIPTION OF RELATED ART

A significant consideration in the production of transgenic plants is obtaining sufficient levels of expression of the transgene in the tissues of interest in a preferential or selective way. In this way, potential drawbacks associated with the constitutive expression of the transcript, such as yield drag, may be avoided. Selection of appropriate promoters is crucial for obtaining the pattern of expression of interest with a particular transgene.

Selective expression of transgenes in roots of plants, particularly cereal plants, such as corn, is considered to be potentially commercially important, e.g. for alteration of the function of root tissue, resistance to pathogens or pests with a preference for attack of roots (such as nematodes, corn rootworm etc.), resistance to herbicides or adverse environmental conditions (such as drought or soil composition).

U.S. Pat. No. 5,633,363 describes a 4.7 kb upstream promoter region designated ZRP2 isolated from maize and attributes a particular utility to this promoter region in driving root preferential expression of heterologous genes.

WO 97/44448 relates generally to mechanisms of gene expression in plants and more specifically to regulation of expression of genes in plants in a tissue-specific manner particularly in roots. A method for isolation of transcriptional regulatory elements that contribute to tissue-preferred gene expression is disclosed.

WO 00/15662 describes a promoter of a glycine rich protein (zmGRP3) whose transcripts accumulate exclusively in roots of young maize seedlings following developmentally specific patterns.

WO 00/070068 and WO 00/70066 describe respectively the maize RS81 and RS324 promoters which are promoters of genes expressed in maize root tissue but not in kernel tissue and in molecular analysis were described to have a root-specific expression profile.

Despite the fact that corn root preferential promoters are available in the art, a need remains for alternative promoters capable of preferential or selective root selective expression, e.g. for the independent expression of several foreign DNA sequences of interest without the possibility of post-transcriptional silencing due to the use of the same promoter. In addition, the known corn root preferential promoters, each direct a particular temporal, spatial and/or developmental expression pattern, which does not always suit particular goals. There remains thus a need for novel corn root preferential promoters with the capacity to control transcription in roots, preferably in a more selective manner, and also preferably resulting in a highly abundant transcription product.

SUMMARY AND OBJECTS OF THE INVENTION

It is an object of the invention to provide corn root preferential promoters comprising a nucleotide sequence selected from the following group of nucleotide sequences:

a. a nucleotide sequence comprising the nucleotide sequence of SEQ ID No 1 from the nucleotide at position 1 to the nucleotide at position 338 or the nucleotide sequence of SEQ ID No 2 from the nucleotide sequence at position 11 to the nucleotide at position 1196 ("GL4 promoter";

b. a nucleotide sequence comprising the nucleotide sequence of SEQ ID No 14 from the nucleotide at position 1 to the nucleotide at position 1280 ("GL5 promoter");

c. a nucleotide sequence comprising the nucleotide sequence of about an 400 bp to an about 1300 bp DNA fragment from the 5' end of a corn root preferential gene encoding a mRNA, from which a cDNA can be prepared that comprises the complement of the nucleotide sequence of SEQ ID No 7 or SEQ ID No 8 or SEQ ID No 9 or SEQ ID No 10;

d. a nucleotide sequence comprising the nucleotide sequence of an about 400 bp to an about 1300 bp DNA fragment from the 5' end of a corn root preferential gene encoding a mRNA from which a cDNA can be prepared that contains a nucleotide sequence encoding a polypeptide with the amino acid of SEQ ID No 4 or 6;

e. a nucleotide sequence comprising the nucleotide sequence of an about 400 bp to an about 1300 bp DNA fragment from the 5' end of a corn root preferential gene encoding a mRNA, from which a cDNA can be prepared that comprises a nucleotide sequence having at least 75%, at least 80%, at least 90%, at least 95%, or is identical to the nucleotide sequence of any of SEQ ID No 3, 5 or 11;

f. a nucleotide sequence comprising the nucleotide sequence having at least 70% at least 80%, at least 90%, at least 95%, or is identical to any of said nucleotide sequence mentioned under a), b), c),d), e), or f) ;or g. a nucleotide sequence comprising the nucleotide sequence of an about 400 bp to an about 1300 bp DNA fragment hybridizing under stringent conditions with a DNA fragment having said nucleotide sequence mentioned under a), b), c), d), e) or f).

The corn root preferential promoters may be comprised within a corn root preferential promoter region, and may further comprise the nucleotide sequence of SEQ ID 1 from the nucleotide at position 339 to the nucleotide at position 366 or the nucleotide sequence of SEQ ID 14 from the nucleotide at position 1281 to the nucleotide at position 1308.

It is another object of the invention to provide chimeric genes comprising the following operably linked DNA regions: a corn root preferential promoter according to the invention; a heterologous DNA region encoding a biologically active RNA of interest; and a transcription termination and polyadenylation signal active in plant cells. The biologically active RNA may encode a protein of interest, such as a protein which when expressed in the cells of a plant confers pest or pathogen resistance to said plant. The biologically active RNA may also be an antisense, sense or double stranded RNA useful for post-transcriptional silencing of a target gene of interest.

Also provided are plant cells and plants or seeds thereof, particularly cereal plants, such as corn plants comprising a chimeric gene according to the invention.

It is yet another objective to provide a method for expressing a biologically active RNA preferentially in the roots of a plant, such as a corn plant, comprising the steps of: providing the cells of the roots of said plants with a chimeric gene according to the invention; and growing the plants.

The invention further provides the use of a corn root preferential promoter according to the invention for preferential expression of a biologically active RNA in roots of a plant, such as a corn plant.

It is yet another object of the invention to provide isolated DNA molecules comprising a nucleotide sequence encoding a protein comprising the amino acid sequence of SEQ ID No 4 or SEQ ID No 6, particularly a nucleotide sequence selected from the group of SEQ ID No 3; SEQ ID No 5 and SEQ ID No 11 and the use thereof for isolation of a corn root preferential promoter or promoter region.

In yet another embodiment the invention provides a method for isolating a corn root preferential promoter region, comprising the steps of: identifying a genomic fragment encoding an RNA transcript from which a cDNA can be synthesized, which cDNA comprises the nucleotide sequence of SEQ ID 3 or SEQ ID No 5 or functional equivalents; and isolating a DNA region upstream of a nucleotide sequence encoding the protein with the amino acid of SEQ ID No 4 or SEQ ID No 6 or functional equivalents. Also provided are corn root preferential promoters obtained by this method.

BRIEF DESCRIPTION OF THE FIGURES

FIG. 1: Alignment of the nucleotide sequences for cDNAs GL4 (SEQ ID NO: 3), GL5 (SEQ ID NO: 5) and GL12 (SEQ ID NO: 11). Gaps in the sequence introduced for optimal alignment are indicated by a dash.

FIG. 2: Nucleotide sequence for the short corn root preferential promoter region from GL4 (SEQ ID NO: 1).

FIG. 3: Nucleotide sequence for the long corn root preferential promoter region from GL4 (SEQ ID NO: 2).

FIG. 4: Nucleotide sequence for the corn root preferential promoter region from GL5 (SEQ ID NO: 14).

DETAILED DESCRIPTION OF EMBODIMENTS OF THE INVENTION

Figure 5:
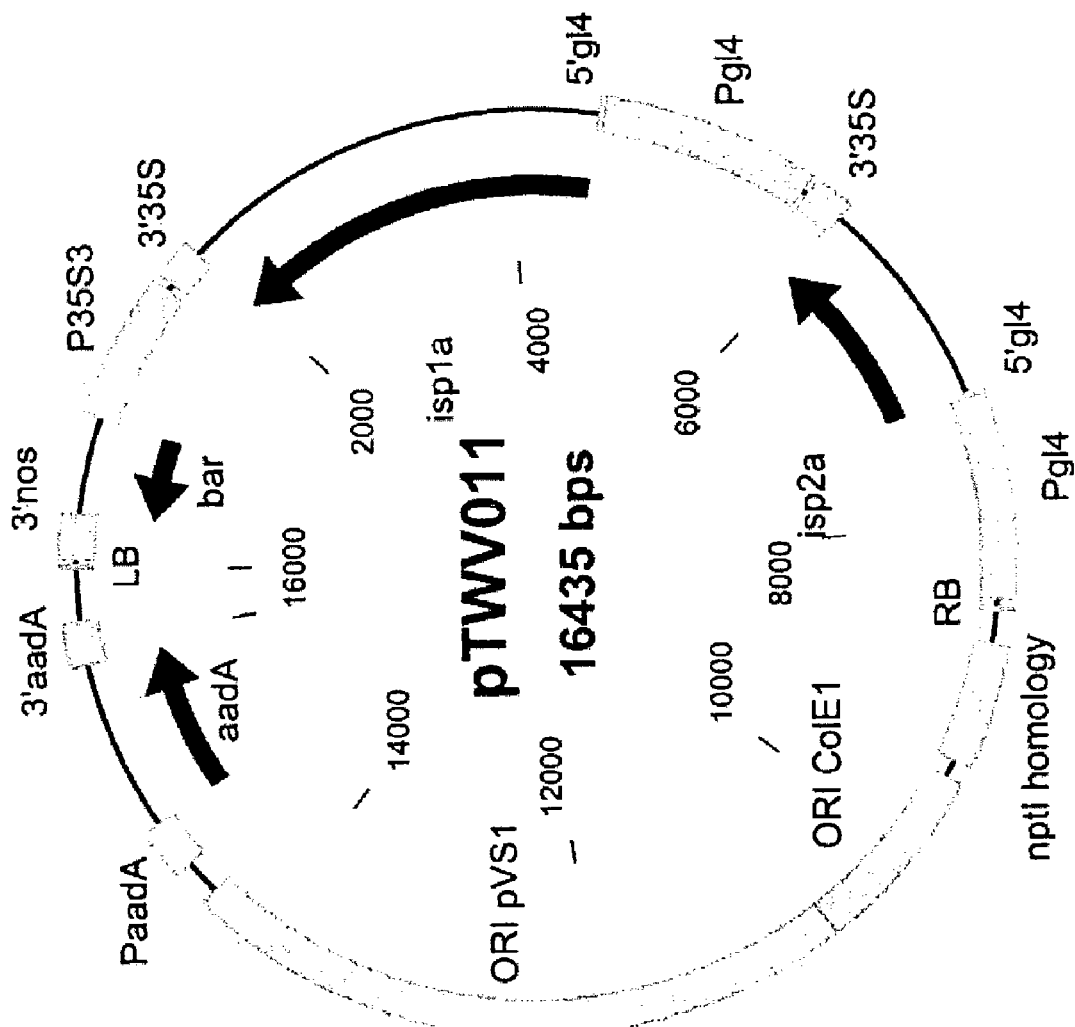
FIG. 5: Schematic representation of pTWV011. LB: left T-DNA border; 3'nos: 3' end of the nopaline synthase gene; bar: bialaphos resistance coding region; P35S3: promoter region of the 35S transcript of CaMV; 3' 35S: 3' end of the 35S transcript of CaMV; isp1a: coding region for insecticidal secreted protein 1a from *Brevibacillus laterosporus;* 5'gl4: leader region of the GL4 promoter region; Pgl4: corn root selective promoter GL4; isp2a: coding region for insecticidal secreted protein 2a from *Brevibacillus laterosporus*; RB: right T-DNA border region; nptl homology: region of homology with helper Ti-plasmids; ORI colE1: colE1 origin of replication; ORI pVS1: origin of replication for Pseudomonas; PaadA: bacterial promoter of the aminoglycoside adenyltransferase conferring resistance to streptomycin and spectinomycin; aadA: coding region of the aminoglycoside adenyltransferase gene; 3' aadA: 3' end of the aminoglycoside adenyltransferase gene.
Figure 6:
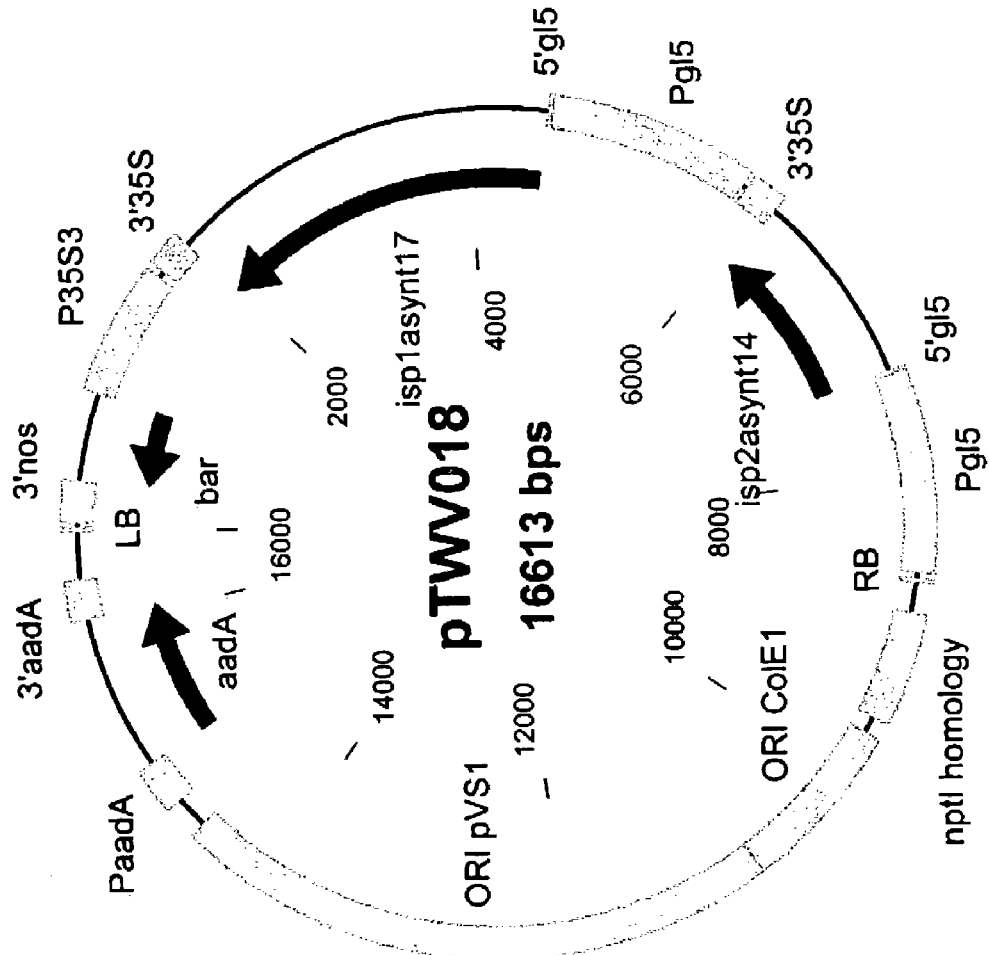
FIG. 6: Schematic representation of pTWV018. LB: left T-DNA border; 3'nos: 3' end of the nopaline synthase gene; bar: bialaphos resistance coding region; P35S3: promoter region of the 35S transcript of CaMV; 3' 35S: 3' end of the 35S transcript of CaMV; isp1a: coding region for insecticidal secreted protein 1a from *Brevibacillus laterosporus;* 5'gl5: leader region of the GL5 promoter region; Pgl5: corn root selective promoter GL5; isp2a: coding region for insecticidal secreted protein 2a from *Brevibacillus laterosporus*; RB: right T-DNA border region; nptl homology: region of homology with helper Ti-plasmids; ORI colE 1: colE1 origin of replication; ORI pVS1: origin of replication for *Pseudomonas*; PaadA: bacterial promoter of the aminoglycoside adenyltransferase conferring resistance to streptomycin and spectinomycin; aadA: coding region of the aminoglycoside adenyltransferase gene; 3' aadA: 3' end of the aminoglycoside adenyltransferase gene.

The invention is based on the finding that the promoters described herein are particularly suited for the preferential and abundant expression (i.e. transcription or transcription and translation) of an operably linked foreign DNA in roots of plants, particularly cereal plants such as corn.

In one embodiment of the invention, a corn root preferential promoter region is provided comprising the nucleotide sequence of SEQ ID 1 of about 400 bp. In another embodiment, a corn root preferential promoter region is provided comprising the nucleotide sequence of SEQ ID No 2 of about 1200 bp. In yet another embodiment, a corn root preferential promoter region is provided comprising the nucleotide sequence of SEQ ID No 14 from the nucleotide at position 1 to the nucleotide at position 1280.

As used herein "corn" refers to maize i.e. *Zea mays* L.

As used herein, the term "promoter" denotes any DNA which is recognized and bound (directly or indirectly) by a DNA-dependent RNA-polymerase during initiation of transcription. A promoter includes the transcription initiation site, and binding sites for transcription initiation factors and RNA polymerase, and can comprise various other sites (e.g., enhancers), at which gene expression regulatory proteins may bind.

The term "regulatory region", as used herein, means any DNA, that is involved in driving transcription and controlling (i.e., regulating) the timing and level of transcription of a given DNA sequence, such as a DNA coding for a protein or polypeptide. For example, a 5' regulatory region (or "promoter region") is a DNA sequence located upstream (i.e., 5') of a coding sequence and which comprises the promoter and the 5'-untranslated leader sequence. A 3' regulatory region is a DNA sequence located downstream (i.e., 3') of the coding sequence and which comprises suitable transcription 3' end formation (and/or regulation) signals, including one or more polyadenylation signals.

The term "gene" means any DNA fragment comprising a DNA region (the "transcribed DNA region") that is transcribed into a RNA molecule (e.g., a mRNA) in a cell under control of suitable regulatory regions, e.g., a plant expressible promoter region. A gene may thus comprise several operably linked DNA fragments such as a promoter, a 5' untranslated leader sequence, a coding region, and a 3' untranslated region comprising a polyadenylation site. An endogenous plant gene is a gene which is naturally found in a plant species. A chimeric gene is any gene which is not normally found in a plant species or, alternatively, any gene in which the promoter is not associated in nature with part or all of the transcribed DNA region or with at least one other regulatory regions of the gene.

The term "expression of a gene" refers to the process wherein a DNA region under control of regulatory regions, particularly the promoter, is transcribed into an RNA which is biologically active, i.e., which is either capable of interaction with another nucleic acid or which is capable of being translated into a biologically active polypeptide or protein. A gene is said to encode an RNA when the end product of the expression of the gene is biologically active RNA, such as an antisense RNA or a ribozyme. A gene is said to encode a protein when the end product of the expression of the gene is a biologically active protein or polypeptide.

The term "root-selective", with respect to the expression of a DNA in accordance with this invention, refers to, for practical purposes, the highly specific, expression of a DNA in cells of roots of plants, such as corn plants ("corn-root-selective"). In other words, transcript levels of a DNA in tissues different of root plants is either below detection or very low (less than about 0.2 picograms per microgram total RNA).

The term "root-preferential" with respect to the expression of a DNA in accordance with this invention, refers to an expression pattern whereby the DNA is expressed predominantly in roots, but expression can be identified in other tissues of the plant. In one embodiment of the present invention, expression in roots may be enhanced by about 2 to about 10 times higher in roots than in other tissues.

It will be clear that having read these embodiments, the person skilled in the art can easily identify and use functional equivalent promoters for the same purposes.

DNA sequences which have a promoter activity substantially similar to the corn root preferential promoters comprising the nucleotide sequence of SEQ ID 1 from the nucleotide at position 1 to the nucleotide at position 338 or SEQ ID 2 from the nucleotide at position 11 to the nucleotide at position 1196 or SEQ ID 14 from the nucleotide at position 1 to the nucleotide at position 1280, or parts thereof having promoter activity, are functional equivalents of these promoters. These functional equivalent promoters may hybridize with the corn root preferential promoter regions comprising the nucleotide sequence of SEQ ID 1 or of SEQ ID No 2 or of SEQ ID 14 under stringent hybridization conditions.

"Stringent hybridization conditions" as used herein means that hybridization will generally occur if there is at least 95% or even at least 97% sequence identity between the probe and the target sequence. Examples of stringent hybridization conditions are overnight incubation in a solution comprising 50% formamide, 5×SSC (150 mM NaCl, 15 mM trisodium citrate), 50 mM sodium phosphate (pH 7.6), 5×Denhardt's solution, 10% dextran sulfate, and 20 µg/ml denatured, sheared carrier DNA such as salmon sperm DNA, followed by washing the hybridization support in 0.1×SSC at approximately 65° C. Other hybridization and wash conditions are well known and are exemplified in Sambrook et al, Molecular Cloning: A Laboratory Manual, Second Edition, Cold Spring Harbor, NY (1989), particularly chapter 11.

Other functional equivalent promoters comprise nucleotide sequences which can be amplified using oligonucleotide primers comprising at least about 25, at least about 50, or at least about 100 consecutive nucleotides selected from the nucleotide sequence of SEQ ID 1 or SEQ ID 2, in a polymerase chain amplification reaction. Examples of such oligonucleotide primers are GVK 29 (SEQ ID No 9) and GVK 30 (SEQ ID No 10).

Functionally equivalent promoters may be isolated e.g. from different corn varieties. They may also be made by modifying isolated corn root-preferential promoters through addition, substitution, deletion or insertion of nucleotides. They can also be completely or partly synthesized.

Alternatively, functional equivalent promoters may be isolated using a cDNA of a transcript which is expressed at a high level in roots of a plant, such as a corn plant, as a probe to isolate the genomic DNA upstream of the nucleotide sequence corresponding to the nucleotide sequence of the cDNA. As used herein "cDNA" is used to indicate both the first strand cDNA (complementary to the mRNA) as well as the strand complementary thereto (and thus identical to the mRNA except that U is replaced by T) or a double stranded cDNA fragment. In accordance with this invention, corn root selective cDNAs and their corresponding plant genomic DNA fragments may be identified as follows:

- a cDNA library may be constructed starting from mRNA isolated from roots and the cDNA library subjected to differential screening in order to identify an mRNA which is preferentially present in roots when compared to other plant tissues including but not limited to: leaves, seeds, stems, reproductive organs, and the like. Alternatively, the cDNA library may screened with oligonucleotides, that are deduced from a determined amino acid sequence of an isolated protein, that has been identified to be preferentially present in the roots. Furthermore, it is possible to use the same oligonucleotides in a nested-PCR approach and to use the amplified fragment(s) as a probe to screen the library. The corn root preferential cDNA library can be constructed from a pool of mRNAs, isolated at different stages of corn root development. One method to identify and isolate the 3' ends of cDNA of RNA particularly expressed in a specific tissue such as here the roots of plants, is the so-called READS analysis or Restriction-Enzyme digested cDNAs as described e.g. by Prashar and Weismann or U.S. Pat. No. 5,712,126 (both documents are herein incorporated by reference).
- A cDNA reverse transcribed from RNA preferentially transcribed in roots of plants, such as corn plants, or 3' ends of cDNAs identified by READS differential display analysis as expressed preferentially in roots of plants may be isolated and further characterized by e.g. nucleotide sequence determination; a full length cDNA may be isolated using e.g. 5' RACE (rapid amplification of cDNA ends) technology.
- This cDNA or the 3' end thereof may be used as a probe to identify and isolate the region in the plant genome, comprising the nucleotide sequence encoding the corn root preferential mRNA. Alternatively, the genomic DNA can be isolated by e.g. inverse PCR using oligonucleotides deduced from the cDNA sequence. Alternatively, TAIL-PCR (thermal assymetric interlaced PCR as described by Liu et al. (1995)) using nested long specific oligonucleotides derived from the nucleotide sequence of the (5' end) of the identified cDNA and a short arbitrary degenerate primer may be used to isolate the genomic sequences flanking the coding region.
- Optionally, RNA probes corresponding to the cDNAs are constructed and used in conventional RNA-RNA in-situ hybridization analysis [see e.g., De Block et al. (1993), *Anal. Biochem.*215: 86] of different plant tissues, including the root tissue of interest, to confirm the preferential presence of the mRNA produced by the endogenous plant gene presumed root preferential expression in those roots.

Once the corn root-prefential gene (i.e., the genomic DNA fragment, encoding the corn root-preferential mRNA from which the corn-root preferential cDNA can be prepared) is obtained, the promoter region containing the corn root-preferential promoter is determined as the region upstream (i.e., located 5' of) from the codon coding for the first amino acid of the protein encoded by the mRNA. It is preferred that such promoter region is at least about 400 to 500 bp, at least about 1000 bp, about 1200 bp, about 1300 bp, or at least about 1500 to 2000 bp, upstream of the start codon. For convenience, such promoter region may not extend more than about 3000 to 5000 bp upstream of the start codon. The size fragment may be partially determined by the presence of convenient restriction sites. The actual corn root-preferential promoter is the region of the genomic DNA upstream (i.e., 5') of the region encoding the corn root-preferential mRNA. A chimeric gene comprising a corn root-preferential promoter operably linked to the coding region of a marker gene will produce the marker protein preferentially in the cells of the corn roots of transgenic corn plants, which can be assayed by conventional in situ histochemical techniques.

Examples of corn root-preferential genes from which corn root-preferential promoters can be obtained, are genes, that encode a mRNA which can be detected preferentially in corn roots and have a size of about 600 nts, from which a cDNA can be prepared that contains the complement of the nucleotide sequence corresponding to the nucleotide sequence of oligonucleotide GVK27 (SEQ ID No 7) and/or the complement of the nucleotide sequence of oligonucleotide GVK28 (SEQ ID No 8); and/or contains the complement of the nucleotide sequence corresponding to the oligonucleotide GVK29 (SEQ ID No 9) and/or contains the complement of the nucleotide sequence corresponding to the oligonucleotide GVK30 (SEQ ID No 10). Such corn root-prefential cDNA may contain each of the aforementioned sequences corresponding to oligonucleotides GVK27 and GVK28 as well as GVK29 or GVK30

Such a gene is the gene that encodes a corn root-preferential transcript from which a cDNA can be prepared that contains a nucleotide sequence encoding the protein with the amino acid sequence of SEQ ID 4 and which may e.g. have the nucleotide sequence of SEQ ID No 3. Other corn root-preferential genes are the genes that encode a corn root-preferential mRNA from which a cDNA can be prepared that contains the sequence of SEQ ID No 5 or SEQ ID 11, or that contains a nucleotide sequence encoding the protein comprising the amino acid sequence of SEQ ID No 6.

One embodiment of a promoter of the present invention is a promoter contained in the 5' regulatory region of a genomic clone comprising a nucleotide sequence corresponding to the cDNA with the nucleotide sequence of any one of SEQ ID No 5, 6 or 11, e.g. the 5' regulatory region with the nucleotide sequence of SEQ ID No 2 from the nucleotide at position 11 to the nucleotide at position 1196 or a DNA fragment comprising the sequence of SEQ ID No 2 starting anywhere between the nucleotide at position 11 to the nucleotide at postion 859, and ending at nucleotide position 1233 (just before the ATG translation start codon) or a DNA fragment comprising the sequence of SEQ ID No 14 from the nucleotide at position 1 to the nucleotide at position 1280. Such a promoter region comprises a corn root-preferential promoter of the invention and the 5' untranslated leader region, and may be used for the construction of root-preferential chimeric genes, particularly corn root preferential chimeric genes. However, smaller DNA fragments can be used as promoter regions in this invention and it is believed that any fragment of the DNA of SEQ ID No 2 which comprises at least the about 400 basepairs upstream from the translation inititation codon can be used.

Artificial promoters can be constructed which contain those internal portions of the promoter of the 5' regulatory region of SEQ ID No 1 or SEQ ID No 2 or SEQ ID 14 that determine the corn root-preference of this promoter. These artifical promoters might contain a "core promoter" or "TATA box region" of another promoter capable of expression in plants, such as a CaMV 35S "TATA box region" as described in WO 93/19188. The suitability of promoter regions containing such artificial promoters may be identified by their appropriate fusion to a reporter gene and the detection of the expression of the reporter gene in the appropriate tissue(s) and at the appropriate developmental stage. It is believed that such smaller promoters and/or artificial promoters comprising those internal portions of the 5' regulatory region of SEQ ID No. 1 or 2 that determine the corn root preference can provide better selectivity of transcription in corn root cells and/or provide enhanced levels of transcription of the transcribed regions of the corn root-preerential chimeric genes of the invention. Such smaller portions of the corn root preferential promoter regions of the invention may include the nucleotide sequences which share a high homology between the GL4 and GL5 promoter regions such as: the nucleotide sequence of SEQ ID No 2 from the nucleotide at position 1024 to the nucleotide at position 1105 (having a 80% match with the nucleotide sequence of SEQ ID No 14 from the nucleotide at position 435 to the nucleotide at position 510); the nucleotide sequence of SEQ ID No 2 from the nucleotide at position 866 to the nucleotide at position 994 (having a 77% match with the nucleotide sequence of SEQ ID No 14 from the nucleotide at position 236 to the nucleotide at position 358); the nucleotide sequence of SEQ ID No 2 from the nucleotide at position 544 to the nucleotide at position 568 (having a 96% match with the nucleotide sequence of SEQ ID No 15 from the nucleotide at position 198 to the nucleotide at position 222); the nucleotide sequence of SEQ ID No 2 from the nucleotide at position 1122 to the nucleotide at position 1143 (having a 73% match with the nucleotide sequence of SEQ ID No 15 from the nucleotide at position 485 to the nucleotide at position 510).

Besides the actual promoter, the 5' regulatory region of the corn root-preferential genes of this invention also comprises a DNA fragment encoding a 5' untranslated leader (5'UTL) sequence of an RNA located between the transcription start site and the translation start site. It is believed that the 5' transcription start site of the GL4 promoter is located around position 1197 in SEQ ID No 2, resulting in a 5'UTL of about 30 nucleotides in length. It is believed that the 5' transcription start site of the GL5 promoter is located around position 1280 in SEQ ID No 14, resulting in a 5'UTL of about 30 nucleotides in length It is also believed that this region can be replaced by another 5'UTL, such as the 5'UTL of another plant-expressible gene, without substantially affecting the specificity of the promoter.

Thus, in another embodiment the invention provides a corn root preferential promoter or corn root preferential promoter region comprising a nucleotide sequence selected from the following group of nucleotide sequences:

a nucleotide sequence comprising the nucleotide sequence of SEQ ID No 1 from the nucleotide at position 1 to the nucleotide at position 338 or the nucleotide sequence of SEQ ID No 2 from the nucleotide sequence at position 11 to the nucleotide at position 1196;

a nucleotide sequence comprising the nucleotide sequence of SEQ ID No 14 from the nucleotide at position 1 to the nucleotide at position 1280;

the nucleotide sequence of about an 400 bp to an about 1300 bp DNA fragment from (the 5' end of) a corn root preferential gene encoding a mRNA, the mRNA having a size of about 600 nt, from which a cDNA can be prepared that contains the complement of the nucleotide sequence corresponding to the nucleotide sequence of SEQ ID No 7, SEQ ID No 8, SEQ ID No 9, or SEQ ID No 10;

the nucleotide sequence of an about 400 bp to an about 1300 bp DNA fragment from the 5' end of a corn root prefential gene encoding a mRNA, the mRNA having a size of about 600 nt, from which a cDNA can be prepared that contains a nucleotide sequence encoding a polypeptide with the amino acid of SEQ ID No 4 or 6;

the nucleotide sequence of an about 400 bp to an about 1300 bp DNA fragment from the 5' end of a corn root preferential gene encoding a mRNA, from which a cDNA can be prepared that comprises a nucleotide sequence having at least 75% or at least 80% or at least 90%, or at least 95% sequence identity with the nucleotide sequence of any of SEQ ID No 3, 5 or 11 or is identical thereto;

the nucleotide sequence having at least 70% or 80% or 90% or 95% sequence identity to any of the nucleotide sequence mentioned under a), b), c),d), e), or f), particularly the nucleotide sequence mentioned under a) or is identical thereto; or the nucleotide sequence of an about 400 bp to an about 1300 bp DNA fragment hybridizing under stringent conditions with a DNA fragment having the nucleotide sequence mentioned under a), b), c), d), e) or f), particularly the nucleotide sequence mentioned under a).

For the purpose of this invention, the "sequence identity" of two related nucleotide or amino acid sequences, expressed as a percentage, refers to the number of positions in the two optimally aligned sequences which have identical residues (×100) divided by the number of positions compared. A gap, i.e. a position in an alignment where a residue is present in one sequence but not in the other, is regarded as a position with non-identical residues. The alignment of the two sequences is performed by the Needleman and Wunsch algorithm (Needleman and Wunsch 1970). The computer-assisted sequence alignment above can be conveniently performed using standard software program such as GAP which is part of the Wisconsin Package Version 10.1 (Genetics Computer Group, Madison, Wis., USA) using the default scoring matrix with a gap creation penalty of 50 and a gap extension penalty of 3.

Promoters and promoter regions of the invention may also comprise additional elements known to improve transcription efficiency such as enhancers, introns, etc.

The invention further includes DNA molecules comprising the corn root preferential promoters of the invention operably linked to one or more heterologous regions coding for a biologically active RNA, peptide or protein. The promoters of the invention may be used to express any heterologous coding region desired.

Thus in another embodiment of the invention, a chimeric gene is provided comprising a. a corn root preferential promoter region; comprising the nucleotide sequence selected from the group consisting of
  i. the nucleotide sequence of SEQ ID No 1 from the nucleotide at position 1 to the nucleotide at position 338 or the nucleotide sequence of SEQ ID No 2 from the nucleotide at position 11 to the nucleotide at position 1196;
  ii. a nucleotide sequence comprising the nucleotide sequence of SEQ ID No 14 from the nucleotide at position 1 to the nucleotide at position 1280;
  iii. the nucleotide sequence of about an 400 bp to an about 1300 bp DNA fragment from (the 5' end of) a corn root preferential gene encoding a mRNA, the mRNA having a size of about 600 nt, from which a cDNA can be prepared that contains the complement of the nucleotide sequence corresponding to the nucleotide sequence of SEQ ID No 7 SEQ ID No 8 or SEQ ID No 9 or SEQ ID No 10;
  iv. the nucleotide sequence of an about 400 bp to an about 1300 bp DNA fragment from the 5' end of a corn root preferential gene encoding a mRNA, the mRNA having a size of about 600 nt, from which a cDNA can be prepared that contains a nucleotide sequence encoding a polypeptide with the amino acid of SEQ ID No 4 or 6;
  v. the nucleotide sequence of an about 400 bp to an about 1300 bp DNA fragment from the 5' end of a corn root preferential gene encoding a mRNA, from which a cDNA can be prepared that comprises a nucleotide sequence having at least 75% or 80% or 90% or 95% sequence identity with the nucleotide sequence of any of SEQ ID No 3, 5 or 11 or is identical thereto;
  vi. the nucleotide sequence having at least 75% or 80% or 90% or 95% sequence identity with the nucleotide sequence mentioned under i), ii), iii),iv), v), or vi), particularly the nucleotide sequence mentioned under i) or is identical thereto; or
  vii. the nucleotide sequence of an about 400 bp to an about 1300 bp DNA fragment hybridizing under stringent conditions with a DNA fragment having the nucleotide sequence mentioned under i), ii), iii), iv), v) or vi), particularly the nucleotide sequence mentioned under a);
b. a DNA region of interest, which when transcribed yields a biologically active RNA; and
c. a DNA region comprising a 3' transcription termination and polyadenylation signal functional in plant cells.

The DNA region of interest, or the transcribed RNA may thus encode a protein or polypeptide, but may also encode biologically active RNA, such as an antisense RNA, a sense RNA, or a dsRNA comprising both sense and antisense RNA stretches capable of basepairing and forming a double stranded RNA, as described in WO 99/53050 (incorporated herein by reference) usable for posttranscriptional gene silencing of a target sequence.

To confer corn rootworm resistance, such as for example resistance to *Diabrotica barberi*, *Diabrotica undecimpunctata*, and/or *Diabrotica virgifera*, to plants, such as corn plants, in a root selective or root preferential way, suitable candidate DNA regions to be operably linked to the corn root selective promoters of the invention include the mature VIP1Aa protein when combined with the mature VIP2Aa or VIP2Ab protein of PCT publication WO 96/10083; the corn rootworm toxins of *Photorhabdus* or *Xhenorhabdus* spp., e.g., the insecticidal proteins of *Photorhabdus luminescens* W-14 (Guo et al., 1999, J. Biol. Chem. 274, 9836–9842); the CryET70 protein of WO 00/26378; the insecticidal proteins produced by Bt strains PS80JJ1, PS149B1 and PS167H2 as described in WO 97/40162, particularly the about 14 kD and about 44 kD proteins of Bt strain PS149B1; the Cry3Bb protein of U.S. Pat. No. 6,023,013; protease inhibitors such as the N2 and R1 cysteine proteinase inhibitors of soybean (Zhao et al., 1996, Plant Physiol. 111, 1299–1306) or oryzastatine such as rice cystatin (Genbank entry S49967), corn cystatin (Genbank entries D38130, D10622, D63342) such as the corn cystatin expressed in plants as described by Irie et al. (1996, Plant Mol. Biol. 30, 149–157). Also included are all equivalents and variants, such as truncated proteins retaining insecticidal activity, of any of the above proteins.

In one embodiment of the invention, chimeric genes for conferring rootworm resistance in a root preferential way comprise a nucleotide sequence encoding an insecticidal secreted protein (ISP) from *Brevibacillus laterosporus*, which is insecticidal when ingested by an insect in combination with an ISP complimentary protein, such as another ISP protein, as described in PCT application PCT/EP01/05702 published as WO 01/87931 (incorporated herein by reference; particularly DNA sequences SEQ ID No7 and 9 of WO 01/87931). The nucleotide sequences encoding ISP protein may be a modified DNA.

The invention further provides methods for expressing a foreign DNA of interest preferentially in the roots of a plant, such as a corn plant, comprising the following steps:

providing plant cells with the chimeric genes of the invention, which may be stably integrated in their genome, e.g. their nuclear genome, to generate transgenic cells; and regenerating plants from said transgenic cells.

A convenient way to provide plant cells with the chimeric genes of the invention is to introduce the DNA via conventional transformation methods. It will be clear that actual method of transforming the plants, particularly cereal plants has little importance for the currently described methods. Several methods for introduction of foreign DNA into the genome of plant cells are available in the art. These methods include, but are not limited to, direct protoplast transformation (see e.g. for corn U.S. Pat. No. 5,792,936, incorporated herein by reference); *Agrobacterium*-mediated transformation (see e.g. for corn U.S. Pat. No. 6,074,877 or U.S. Pat. No. 6,140,553 incorporated herein by reference); microprojectile bombardment, electroporation of compact embryogenic calli (see e.g. for corn U.S. Pat. No. 5,641,664 incorporated herein by reference); or silicon whisker mediated DNA introduction.

Operably linking the foreign DNA of interest to a corn root preferential promoter according to the invention may also be achieved by replacing the DNA naturally associated with the corn root preferential promoter by homologous recombination with the DNA of interest, provided that said DNA of interest comprises a homology region with the DNA normally associated with the corn root preferential promoter. Methods for introducing DNA of interest into plant cell genome by homologous recombination are available (e.g. U.S. Pat. No. 5,744,336 incorporated herein by reference).

The obtained transformed plant can be used in a conventional breeding scheme to produce more transformed plants with the same characteristics or to introduce the chimeric gene for corn root preferential expression according to the invention in other varieties of the same or related plant species, or in hybrid plants. Seeds obtained from the transformed plants contain the chimeric genes of the invention as a stable genomic insert and are also encompassed by the invention.

It will be appreciated that the means and methods of the invention are particularly useful for corn, but may also be used in other plants with similar effects, particularly in cereal plants including corn, wheat, oat, barley, rye, rice, turfgrass, sorghum, millet or sugarcane plants.

The following non-limiting Examples describe the isolation of corn root preferential promoters, and the construction of chimeric genes for selective expression in corn root plants. Unless stated otherwise in the Examples, all recombinant DNA techniques are carried out according to standard protocols as described in Sambrook et al. (1989) *Molecular Cloning: A Laboratory Manual*, Second Edition, Cold Spring Harbor Laboratory Press, NY and in Volumes 1 and 2 of Ausubel et al. (1994) *Current Protocols in Molecular Biology, Current Protocols*, USA. Standard materials and methods for plant molecular work are described in*Plant Molecular Biology Labfax* (1993) by R. D. D. Croy, jointly published by BIOS Scientific Publications Ltd (UK) and Blackwell Scientific Publications, UK.

Throughout the description and Examples, reference is made to the following sequences represented in the sequence listing.

SEQ ID No 1: nucleotide sequence of the about 400 bp corn root preferential promoter (GL4 promoter).
SEQ ID No 2: nucleotide sequence of the about 1200 bp corn root preferential promoter (GL4 promoter).
SEQ ID No 3: nucleotide sequence of the cDNA of the naturally associated mRNA transcribed under control of the corn root preferential promoter having the nucleotide sequence of SEQ ID No 1 (GL4).
SEQ ID No 4: amino acid sequence of the protein encoded by the cDNA GL4.
SEQ ID No 5: nucleotide sequence of the corn root preferential cDNA GL5.
SEQ ID No 6: amino acid sequence of the protein encoded by the cDNA GL5.
SEQ ID No 7: oligonucleotide primer GVK 27.
SEQ ID No 8: oligonucleotide primer GVK28.
SEQ ID No 9: oligonucleotide primer GVK 29.
SEQ ID No 10: oligonucleotide primer GVK 30.
SEQ ID No 11: nucleotide sequence of corn root preferential cDNA GL12.
SEQ ID No 12: nucleotide sequence of plasmid pTWV011.
SEQ ID No 13: nucleotide sequence of plasmid pTWV018.
SEQ ID No 14: nucleotide sequence of the about 1300 bp corn root preferential promoter (GL5 promoter).
SEQ ID No 15: oligonucleotide primer GVK22.
SEQ ID No 16: oligonucleotide primer GVK23.
SEQ ID No 17: oligonucleotide primer GVK24.
SEQ ID No 18: oligonucleotide primer GVK25.
SEQ ID No 19: oligonucleotide primer GVK26.
SEQ ID No 20: oligonucleotide primer GVK31.
SEQ ID No 21: oligonucleotide primer GVK32.
SEQ ID No 22: oligonucleotide primer GVK33.
SEQ ID No 23: oligonucleotide primer GVK38.
SEQ ID No 24: oligonucleotide primer GVK39.
SEQ ID No 25: oligonucleotide primer GVK45.
SEQ ID No 26: oligonucleotide primer MDB285.
SEQ ID No 27: oligonucleotide primer MDB286.
SEQ ID No 28: oligonucleotide primer MDB363.
SEQ ID No 29: oligonucleotide primer MDB364.
SEQ ID No 30: oligonucleotide primer MDB552.
SEQ ID No 31: oligonucleotide primer MDB556.

EXAMPLES

Example 1

Isolation of Root Preferential Corn cDNAs

RNA transcript tags which are expressed preferentially in maize roots were identified by a differential RNA cDNA display known as READS (Prashar and Weismann, 1999, *Methods in Enzymology* 303:258–272).

To this end, total RNA samples were prepared from different tissues (roots, stems, leaves, . . . ) of corn plants, harvested at different developmental stages (from 64 day old plants to adult plants). 3' end fragments of cDNA molecules digested by different endorestriction nucleases were amplified using stringent PCR conditions and oligonucleotides as described by Prashar and Weismann (1999, supra) for each of the samples.

Comparison of gel patterns of the 3' end cDNA restriction fragments generated for each of the RNA samples allowed a preliminary identification of fragments which appeared only in the corn root tissue RNA sample or were more prominent in root tissue RNA than in other corn tissue. These 3' end fragments were isolated and sequenced. Their nucleotide sequence was compared against public and proprietary databases and only novel sequences were used in a further Northern analysis using the RNA samples from different corn tissues as a driver and each of the isolated 3' end cDNA fragments as a probe. The hybridizing RNA transcripts were analyzed for size, abundance, and specificity. The results for the 3' end with the best specificity for expression in corn roots are summarized in Table 1, arranged in descending order of specificity and abundance.

The 3' ends which hybridized to the most abundant RNA transcripts with the highest specific expression in corn roots (GL4; GL5 and GL12) were further analyzed.

For GL4 and GL5 full length cDNAs were isolated using the SMART™ RACE cDNA amplification kit from CLONTECH Laboratories with nested oligonucleotide primers GVK22 (SEQ ID No 15)/GVK23 (SEQ ID No 16) for GL4 and GVK24 (SEQ ID No 17)/GVK25 (SEQ ID No 18) for GL5 The nucleotide sequence of the full length cDNAs is represented in SEQ ID 3 and 5 respectively. Comparison of both nucleotide sequences revealed that GL4 and GL5 have about 89% sequence identity.

TABLE 1

| Identification of 3' end used as probe | Quantification of hybridizing transcript[1] | Estimated length of hybridizing transcript[2] | Specificity of presence of the hybridizing transcript |
| --- | --- | --- | --- |
| GL4 | 18 | About 600 | Root selective |
| GL5 | 15 | About 600 | Root selective |
| GL12 | 13 | About 600 | Root selective |
| GL11 | 3 | About 820 | Root selective |
| GL3 | 1 | About 1200 | Root selective |
| GL9 | 7 | About 900 | Root preferential |
| GL7 | 2 | About 700 | Root preferential |
| GL16 | <2 | About 1500 | Low expression |
| GL17 | <2 | About 650 | Low expression |
| GL6 | — | — | No visible hybridization |

[1]expressed in picogram/μg total RNA
[2]in nucleotide

In both sequences, a small ORF could be identified (starting from the nucleotide of SEQ ID 3 at position 32 to the nucleotide at position 319 for GL4; the nucleotide of SEQ ID 5 at position 27 to the nucleotide at position 307 for GL5). The amino acid sequences of the polypeptides encoded by the ORFs are represented in SEQ ID No 4 or 6. The nucleotide sequence in the region encoding the ORF is more conserved between GL4 and GL5 cDNA than elsewhere in the fragments.

Using the GL4 cDNA nucleotide sequence as a query, a nucleotide sequence has been identified with 91% sequence identity in the 322-nucleotide overlap (SEQ ID No 19 from WO 00/32799). It has not been described that SEQ ID No 19 from *Zea mays* as described in WO 00/32799 is transcribed in a root selective or root preferential way. Further, a nucleotide sequence (clone MEST23-CO7.T3 from a seedling and silk cDNA library) has been identified having 99% sequence identity over 582 nt.

Using the GL5 cDNA nucleotide sequence as a query, a nucleotide sequence has been identified with 85% sequence identity with FtsZ1 related sequence from *Zea mays* (A47325 in Geneseq). It has not been described that this sequence is transcribed in a root selective or root preferential way. Further, a nucleotide sequence (clone MEST523-G12 (3') from a seedling and silk cDNA library) has been identified having 100% sequence identity over 525 nt.

Example 2

Isolation of Corn Root Preferential Promoter Regions of the Gene Transcribing a mRNA, the cDNA of which Corresponds to GL4 or GL5 cDNA.

The genomic fragments upstream of the nucleotide sequences corresponding to GL4 cDNA and GL5 cDNA sequences, comprising the promoter region were isolated using Thermal Asymmetric Interlaced PCR as described by Liu et al (1995, *The Plant Journal* 8(3): 457–463)

Corn genomic DNA for use as the initial template DNA was purified as described by Dellaporte et al. The sequence of the specific nested oligonucleotides used for TAIL-PCR to isolate the genomic fragments located upstream of the genomic DNA sequences corresponding to GL4 cDNA sequences are represented in SEQ ID No 7 (GVK27), SEQ ID No 8 (GVK28) and SEQ ID No 9 (GVK 29); the aspecific degenerate primers used were each of the 6 degenerate primers MDB285, MDB286, MDB363, MDB364, MDB552 or MDB556 in separate reactions. PCR conditions were as described in Liu et al (1995, supra).

A genomic fragment of about 400 bp (corresponding to the amplification product obtained with the primer pair (GVK29/MDB285) was isolated, cloned in pGEM-T Easy ® and sequenced.

Based on the nucleotide sequence of the about 400 bp fragment, new specific nested primer oligonucleotides (GVK 31/SEQ ID No 20; GVK32/SEQ ID No 21 and GVK33/SEQ ID No 22) were designed and used in conjunction with the above mentioned degenerated primers to isolate the adjacent DNA regions further upstream of the isolated promoter region fragment. This resulted in isolation of an about 350 nt DNA fragment (corresponding to the amplification product obtained with the primer pair GVK33/MDB286) In a third round, the adjacent upstream DNA fragment of about 800 nt was isolated using new set of specific nested oligonucleotides GVK33/SEQ ID No 22; GVK38/SEQ ID No 23 and GVK39/SEQ ID No 24 in conjunction with the above mentioned degenerated primers (corresponding to the amplification product using GVK39 and MDB363).

To confirm the continuity of the isolated genomic upstream fragments, the complete 1200 bp DNA fragment was amplified using GVK29 and GVK45 (SEQ ID 25) primers and cloned in pGEM-T Easy®. The complete nucleotide sequence of the about 1200 bp upstream DNA fragment is represented in SEQ ID 2.

Primers GVK 27, GVK28 and GVK30 (SEQ ID No 10) were used in conjunction with the above mentioned degenerated primers. An about 1300 nt fragment was amplified having the sequence of SEQ ID 14 (corresponding to the amplification product by MDB364 and GVK30).

Example 3

Construction of Chimeric Genes using the Isolated GL4/GL5 Corn Root Preferential Promoter Regions.

The following chimeric ISP1A/ISP2A constructs under the control of GL4 promoter region or under control of the GL5 promoter region were made using standard recombinant DNA methods:

GL4::ISP1A comprising the following DNA fragments:
the GL4 promoter region (SEQ ID No 2);
a DNA fragment encoding the isp1A protein of *Brevibacillus laterosporus* (complement of the nucleotide sequence of SEQ ID 12 from the nucleotide at position 2003 to the nucleotide at position 4511);
the 3' end fragment of the 35S transcript (complement of the nucleotide sequence of SEQ ID No 12 from the nucleotide at position 1767 to the nucleotide at position 1991).

GL4::ISP2A comprising the following DNA fragments:

the GL4 promoter region (SEQ ID No 2);

a DNA fragment encoding the isp2A protein of *Brevibacillus laterosporus* (complement of the nucleotide sequence of SEQ ID 12 from the nucleotide at position 6001 to the nucleotide at position 7228); and the 3' end fragment of the 35S transcript (complement of the nucleotide sequence of SEQ ID No 12 from the nucleotide at position 5765 to the nucleotide at position 5989).

GL5::ISP1A comprising the following DNA fragments:

the GL5 promoter region (complement of the nucleotide sequence of SEQ ID No 13 from the nucleotide at position 4518 to the nucleotide at position 5822);

a DNA fragment encoding the ispA1 protein of *Brevibacillus laterosporus* (complement of the nucleotide sequence of SEQ ID 13 from the nucleotide at position 2003 to the nucleotide at position 4511); and the 3' end fragment of the 35S transcript (complement of the nucleotide sequence of SEQ ID No 13 from the nucleotide at position 1767 to the nucleotide at position 1991).

GL5::ISP2A comprising the following DNA fragments:

the GL5 promoter region (complement of the nucleotide sequence of SEQ ID No 13 from the nucleotide at position 8628 to the nucleotide at position 7324);

a DNA fragment encoding the isp2A protein of *Brevibacillus laterosporus*(complement of the nucleotide sequence of SEQ ID 12 from the nucleotide at position 6090 to the nucleotide at position 7317); and the 3' end fragment of the 35S transcript (complement of the nucleotide sequence of SEQ ID No 12 from the nucleotide at position 5765 to the nucleotide at position 5989).

Example 4

Expression Analysis of Chimeric Genes Comprising the GL4 and GL5 Promoters in Stably Transformed Corn Plants.

The chimeric genes described in Example 3 were introduced in a T-DNA vector along with a chimeric bar gene (such as described in U.S. Pat. No. 5,561,236) to yield pTWV011 (GL4 promoter constructs) and pTWV018 (GL5 promoter constructs). These T-DNA vectors were introduced in *Agrobacterium tumefaciens* containing the helper Ti-plasmid pGV4000 or pEHA101.

Corn plants stably transformed with the mentioned chimeric genes were obtained using the *Agrobacterium*-mediated transformation technique described in U.S. Pat. No. 6,140,553.

Corn plants stably transformed with the mentioned chimeric genes may also be obtained using direct DNA delivery to corn protoplast as described in U.S. Pat. No. 5,767,367.

RNA was isolated from root, leaf and stem tissue of these corn plants (grown either in vitro or in vivo) and submitted to Northern analysis using a ISP1A specific probe. The individual results are represented in Table 3.

In summary, after correction for loading by hybridization with ribosomal RNA probe, the GL5 promoter region on average initiated 11 times more transcription in roots than in leaves and 19 times more in roots than in stems.

The GL4 promoter region on average initiates 2 times more transcription in roots than in leaves and more than 10 times more in roots than in stems (although individual transformants may exhibit a more pronounced corn root selective expression pattern).

TABLE 2

Summary of GL4/GL5 transcription data

| | | mean n = 3 | SD | | |
|---|---|---|---|---|---|
| Gl4 promoter | root | 1.25 | 1.18 | root/leaf | 2 |
| | leaf | 0.61 | 0.73 | root/stem | >10 |
| | stem | <0.06 | | | |
| Gl5 promoter | root | 1.32 | 0.24 | root/leaf | 11 |
| | leaf | 0.12 | 0.05 | root/stem | 19 |
| | stem | 0.07 | 0.03 | | |

TABLE 3

Summary of Northern analysis data

| | Corn line | | | Isp1a mRNA (pg/µg tot. RNA) |
|---|---|---|---|---|
| pTWV018 GL5 promoter | | | | |
| 1 | G2ZM3598-004 | root | in vitro | 1.07 |

TABLE 3-continued Summary of Northern analysis data

| Corn line | | | | Isp1a mRNA (pg/μg tot. RNA) | | |
|---|---|---|---|---|---|---|
| 2 | | root | } in vivo | 1.57 | | |
| 3 | | leaf | | 0.15 | root/leaf | 10.2 |
| 4 | | stem | | 0.06 | root/stem | 26.2 |
| 5 | G2ZM3595-014 | root | in vitro | 2.17 | | |
| 6 | | root | } in vivo | 1.10 | | |
| 7 | | leaf | | 0.15 | root/leaf | 7.3 |
| 8 | | stem | | 0.10 | root/stem | 11 |
| 9 | G2ZM3595-018 | root | in vitro | 1.39 | | |
| 10 | | root | } in vivo | 1.28 | | |
| 11 | | leaf | | 0.07 | root/leaf | 18.3 |
| 12 | | stem | | 0.04 | root/stem | 32 |
| 13 | G2ZM3596-016 | root | in vitro | 0.73 | | |
| 14 | | root | } in vivo | <0.06 | | |
| 15 | | leaf | | <0.06 | root/leaf | nd |
| 16 | | stem | | <0.06 | root/stem | nd |
| pTWV011 GL4 promoter | | | | | | |
| 1 | G2ZM3592-029 | root | in vitro | 0.53 | | |
| 2 | | root | } in vivo | 0.72 | | |
| 3 | | leaf | | 0.08 | root/leaf | 9 |
| 4 | | stem | | <0.06 | root/stem | >12 |
| 5 | G2ZM3592-030 | root | in vitro | 1.45 | | |
| 6 | | root | } in vivo | 2.60 | | |
| 7 | | leaf | | 1.45 | root/leaf | 1.8 |
| 8 | | stem | | <0.06 | root/stem | >43 |
| 9 | G2ZM3593-002 | root | in vitro | 0.34 | | |
| 10 | | root | } in vivo | 0.43 | | |
| 11 | | leaf | | 0.31 | root/leaf | 1.4 |
| 12 | | stem | | <0.06 | root/stem | >7.2 |

Example 5

Expression Analysis of Chimeric Genes Comprising the GL4 and GL5 Promoters in Progeny of Stably Transformed Corn Plants.

Nine transgenic T0 lines of each of the GL4 and GL5 promoter containing corn plants of Example 4 were crossed with untransformed B73, and the T1 plants were analyzed by Southern blot, Northern blot and by ELISA assay for the presence of ISP1 mRNA or protein in various plant parts.

Southern analysis was performed at the V4 stage to determine the copy number of the transgenes. All analyzed events were single copy events except two lines that contained 2 copies of the transgene.

Northern analysis was performed on RNA derived from root, leaf and stem material obtained at the V11–V13 stage as in Example 4. Transcript levels were quantified using image quant analysis. A correction for loading differences was performed using a ribosomal probe.

For the plants with the GL4 promoter containing transgene, isp1 mRNA was estimated between 0.17 to 0.74 pg/μg total RNA. The average isp1a mRNA level in roots (n=9) was 0.42 pg/μg total RNA (SE=0.18). The average ratio (n=9) of isp1a mRNA in root versus leaf is >6.3. The average ratio (n=8) of isp1a mRNA in root versus stem is >7.1. No expression was seen in stem, except for one sample where the ratio root/stem was 1.9.

For the plants with the GL5 promoter containing transgene, isp1 mRNA was estimated between 0.95 to 2.55 pg/μg total RNA. The average isp1a mRNA level in roots (n=9) was 1.57 pg/μg total RNA (SE=0.53). The average ratio (n=9) of isp1a mRNA in root versus leaf is >17.6. The average ratio (n=8) of isp1a mRNA in root versus stem is >26.6. No expression was observed in stem.

Root, leaf and stem material, harvested at the V8 stage, was analyzed at the protein level for the presence of ISP1a protein by ELISA. Two plants per event were analyzed. As a negative control, root leaf and stem for wtB73 was checked for ISP1A protein. No ISP1A protein was detected in the control experiments.

For all events no ISP1A protein expression was detected in leaves or stem. The mean value of levels of ISP1A protein detected in roots were:

0.07 μg/ml corresponding to about 0.024% of total protein level (n=18) for roots of plants containing the GL4 promoter driven transgene.

0.12 μg/ml corresponding to about 0.041% of total protein level (n=18) for roots of plants containing the GL5 promoter driven transgene.

Root, leaf, stem and pollen material, harvested at the flowering stage, was analyzed at the protein level for the presence of ISP1a protein by ELISA. One plant per event was analyzed. As a negative control, root, leaf, stem and pollen material for wtB73 was checked for ISP1A protein. No ISP1A protein was detected in the control experiments.

For all events, no ISP1A protein expression was detected in pollen.

Mean ISP1A Protein level detected in root, leaf and stem of plants containing the GL4 promoter driven transgene: mean value (n=9)
root: 0.286 μg isp1a/ml ~0.116% isp1a of tot. protein level
leaf: 0.018 μg isp1a/ml ~0.0022% isp1a of tot. protein level (6% of root level)
stem: 0.020 μg isp1a/ml ~0.0043% isp1a of tot. protein level (7% of root level)

Mean ISP1A Protein level detected in root, leaf and stem of plants containing the GL4 promoter driven transgene mean value (n=9):
root: 0.265 μg isp1A/ml ~0.142% isp1a of tot. protein level
leaf: 0.013 μg isp1A/ml ~0.0015% isp1a of tot. protein level (5% of root level)
stem: 0.024 μg isp1A/ml ~0.0058% isp1a of tot. protein level (9% of root level)

At seed setting, ISP1A protein level was determined in kernels of the transgenic plants. No ISP1A protein could be detected in seed of the transgenic plants, nor in the wt B73 control.

---

What is claimed is:

1. An isolated corn root preferential promoter fragment comprising
the nucleotide sequence of SEQ ID NO: 1 from the nucleotide at position 1 to the nucleotide at position 338 or SEQ ID NO: 2 from the nucleotide sequence at position 11 to the nueleotide at position 1196.

2. An isolated corn root preferential promoter region comprising a corn root preferential promoter according to claim 1.

3. The isolated corn root preferential promoter region according to claim 2, further comprising the nucleotide sequence of SEQ ID NO: 1 from the nucleotide at position 339 to the nucleotide at position 366.

4. The isolated corn root preferential promoter region according to claim 2, further comprising the nucleotide sequence of SEQ ID NO: 14 from the nucleotide at position 1281 to the nucleotide at position 1308 or the complement of the nucleotide sequence of SEQ ID NO: 13 from the nucleotide at position 4518 to the nucleotide at position 4542.

5. A chimeric gene comprising the following operably linked DNA regions
a) a corn root preferential promoter according to claim 1;
b) a heterologous DNA region encoding a biologically active RNA of interest; and
c) a transcription termination and polyadenylation signal.

6. The chimeric gene according to claim 5, wherein said biologically active RNA encodes a protein of interest.

7. The chimeric gene according to claim 6, wherein said protein is a protein which when expressed in the cells of a plant confers pest or pathogen resistance to said plant.

8. The chimeric gene according to claim 7, wherein said protein is ISP1A or ISP2A from *Brevibacillus laterosporus*.

9. A plant cell comprising a chimeric gene according to any one of claims 5 to 8.

10. A plant comprising in its cells a chimeric gene according to any of claims 5 to 8.

11. The plant according to claim 10, which is a corn plant.

12. A seed of a plant comprising in its cells a chimeric gene according to any one of claims 5 to 8.

13. A method for expressing a biologically active RNA preferentially in the roots of a corn plant, said method comprising
a) introducing into the cells of the roots of said corn plant a chimeric gene according to any one of claims 5 to 8; and
b) growing said corn plant.

* * * * *